United States Patent
Baldwin et al.

(10) Patent No.: US 11,826,440 B2
(45) Date of Patent: *Nov. 28, 2023

(54) THERMAL-STABLE WHIPPED FORMULATIONS

(71) Applicants: FORMULATED SOLUTIONS, LLC, Largo, FL (US); BEIERSDORF AG, Hamburg (DE)

(72) Inventors: Stephen Baldwin, Flanders, NJ (US); Scott Carpenter, Palm Harbor, FL (US); Nanhye Kim, New Providence, NJ (US); Tom Meyer, Germantown, TN (US); Jerry Vancleave, Lakeland, TN (US); Eric Dann, Safety Harbor, FL (US); Thomas Dann, Palm Harbor, FL (US); Renee Nelson, Brandon, FL (US); Brian Dann, Clearwater, FL (US)

(73) Assignees: FORMULATED SOLUTIONS, LLC, Largo, FL (US); BEIERSDORF AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/300,245

(22) PCT Filed: May 11, 2017

(86) PCT No.: PCT/US2017/032277
§ 371 (c)(1),
(2) Date: Nov. 9, 2018

(87) PCT Pub. No.: WO2017/197193
PCT Pub. Date: Nov. 16, 2017

(65) Prior Publication Data
US 2019/0151207 A1    May 23, 2019

Related U.S. Application Data

(60) Provisional application No. 62/334,880, filed on May 11, 2016, provisional application No. 62/396,431, filed on Sep. 19, 2016.

(51) Int. Cl.
*A61K 8/04* (2006.01)
*A61K 8/34* (2006.01)
(Continued)

(52) U.S. Cl.
CPC ............. *A61K 8/046* (2013.01); *A23P 30/40* (2016.08); *A61K 8/042* (2013.01); *A61K 8/19* (2013.01); *A61K 8/25* (2013.01); *A61K 8/31* (2013.01); *A61K 8/34* (2013.01); *A61K 8/342* (2013.01); *A61K 8/345* (2013.01); *A61K 8/347* (2013.01); *A61K 8/35* (2013.01); *A61K 8/40* (2013.01); *A61K 8/44* (2013.01); *A61K 8/498* (2013.01); *A61K 8/58* (2013.01); *A61K 8/731* (2013.01); *A61K 8/8152* (2013.01); *A61K 8/8182* (2013.01); *A61K 8/892* (2013.01);
(Continued)

(58) Field of Classification Search
CPC ...... A61K 8/046; A61K 9/0014; A61K 47/02; A61K 47/10; A61K 47/44; A61K 9/06; A61K 8/042; A61K 8/19; A61K 8/25; A61K 8/31; A61K 8/34; A61K 8/345; A61K 8/347; A61K 8/35; A61K 8/40; A61K 8/44; A61K 8/498; A61K 8/58; A61K 8/8152; A61K 8/8182; A61K 8/892; A61K 8/922; A61K 8/342; A61K 8/731; A61K 2800/524; A61K 2800/22; A61K 2800/87; B65D 83/752; A61Q 5/06; A61Q 7/00; A61Q 19/004; A61Q 11/00; A61Q 17/04; A23P 30/40
See application file for complete search history.

(56) References Cited

U.S. PATENT DOCUMENTS

| | | | |
|---|---|---|---|
| 3,395,215 | A | 7/1968 | Schubert et al. |
| 3,710,538 | A | 1/1973 | Lowy |

(Continued)

FOREIGN PATENT DOCUMENTS

| | | | |
|---|---|---|---|
| AU | 2017263531 | A1 | 10/2018 |
| AU | 2017263533 | A1 | 10/2018 |

(Continued)

OTHER PUBLICATIONS

English translation of Blatt et al. (EP 2319586 A1) (Year: 2011).*
International Search Report and Written Opinion received in PCT/US2017/032292 dated Jul. 26, 2017, pp. 10.
International Preliminary Report received in PCT/US2017/032292 dated Nov. 13, 2018, pp. 7.
Aurena Laboratories "SunScreen Bag on Valve", Retrieved from the Internet, Nov. 19, 2014, pgs.
International Search Report and Written Opinion received in PCT/US2017/032277 dated Aug. 1, 2017, pp. 15.
International Preliminary Report received in PCT/US2017/032277 dated Nov. 13, 2018, pp. 10.

(Continued)

*Primary Examiner* — Robert A Wax
*Assistant Examiner* — Quanglong N Truong
(74) *Attorney, Agent, or Firm* — Liang & Hennessey LLP; Stanley D. Liang

(57) ABSTRACT

The present disclosure relates to, inter alia, a formulation comprising one or more active agents and one or more thermal stabilizing agents and is co-mingled with a first propellant that is a gas propellant prior to being filled under pressure into said package; the first propellant is added in sufficient amounts to be dispersed in the formulation; the package is under sufficient pressure suitable to expel the formulation as a whipped formulation upon application of external force on said formulation in said package. The present disclosure also relates to, inter alia, a method of preparing the disclosed formulation; a package comprising the disclosed formulation, and a method of using the disclosed formulation.

13 Claims, 10 Drawing Sheets

(51) Int. Cl.

| | | |
|---|---|---|
| *A61K 8/73* | (2006.01) | |
| *A61Q 17/04* | (2006.01) | |
| *B65D 83/14* | (2006.01) | |
| *A61Q 5/06* | (2006.01) | |
| *A61Q 7/00* | (2006.01) | |
| *A23P 30/40* | (2016.01) | |
| *A61Q 19/00* | (2006.01) | |
| *A61Q 11/00* | (2006.01) | |
| *A61K 9/00* | (2006.01) | |
| *A61K 47/02* | (2006.01) | |
| *A61K 47/10* | (2017.01) | |
| *A61K 47/44* | (2017.01) | |
| *A61K 9/06* | (2006.01) | |
| *A61K 8/19* | (2006.01) | |
| *A61K 8/25* | (2006.01) | |
| *A61K 8/31* | (2006.01) | |
| *A61K 8/35* | (2006.01) | |
| *A61K 8/40* | (2006.01) | |
| *A61K 8/44* | (2006.01) | |
| *A61K 8/49* | (2006.01) | |
| *A61K 8/58* | (2006.01) | |
| *A61K 8/81* | (2006.01) | |
| *A61K 8/892* | (2006.01) | |
| *A61K 8/92* | (2006.01) | |

(52) U.S. Cl.
CPC ............ *A61K 8/922* (2013.01); *A61K 9/0014* (2013.01); *A61K 9/06* (2013.01); *A61K 47/02* (2013.01); *A61K 47/10* (2013.01); *A61K 47/44* (2013.01); *A61Q 5/06* (2013.01); *A61Q 7/00* (2013.01); *A61Q 11/00* (2013.01); *A61Q 17/04* (2013.01); *A61Q 19/004* (2013.01); *B65D 83/752* (2013.01); *A61K 2800/22* (2013.01); *A61K 2800/524* (2013.01); *A61K 2800/87* (2013.01)

(56) References Cited

U.S. PATENT DOCUMENTS

| | | |
|---|---|---|
| 3,970,584 A | 7/1976 | Hart et al. |
| 4,670,272 A | 6/1987 | Chen et al. |
| 5,104,987 A | 4/1992 | King |
| 5,214,925 A | 6/1993 | Hoy et al. |
| 5,560,859 A | 10/1996 | Hartmann et al. |
| 5,858,343 A | 1/1999 | Szymczak |
| 6,322,776 B1 | 11/2001 | Ortega |
| 7,070,722 B1 | 7/2006 | Gilchrist et al. |
| 2004/0052826 A1 | 3/2004 | Fernandez-Kleinlein et al. |
| 2004/0197270 A1 | 10/2004 | Mundschenk |
| 2004/0241099 A1 | 12/2004 | Popp et al. |
| 2004/0247534 A1 | 12/2004 | Stoltz |
| 2004/0258627 A1 | 12/2004 | Riedel et al. |
| 2004/0258628 A1 | 12/2004 | Riedel et al. |
| 2005/0079142 A1 | 4/2005 | Brunckhorst et al. |
| 2008/0017671 A1 | 1/2008 | Shieh et al. |
| 2008/0138296 A1 | 6/2008 | Tamarkin et al. |
| 2008/0253973 A1 | 10/2008 | Tamarkin et al. |
| 2008/0260655 A1 | 10/2008 | Tamarkin et al. |
| 2011/0281827 A1 | 11/2011 | Tamarkin et al. |
| 2012/0087872 A1 | 4/2012 | Tamarkin et al. |
| 2012/0213712 A1 | 8/2012 | Kasai et al. |
| 2012/0288462 A1 | 11/2012 | Lebok et al. |
| 2012/0288465 A1 | 11/2012 | Loechel |
| 2012/0301422 A1 | 11/2012 | Meyer |
| 2013/0011341 A1 | 1/2013 | Nguyen et al. |
| 2013/0233310 A1 | 9/2013 | Hilgers et al. |
| 2014/0030198 A1 | 1/2014 | Fares et al. |
| 2014/0079648 A1 | 3/2014 | Cohen |
| 2014/0120039 A1 | 5/2014 | Baldwin et al. |
| 2014/0131395 A1 | 5/2014 | Chang |
| 2016/0101051 A1 | 4/2016 | Tamarkin et al. |
| 2016/0202051 A1 | 7/2016 | Heist et al. |
| 2019/0142709 A1 | 5/2019 | Baldwin et al. |
| 2019/0282463 A1 | 9/2019 | Baldwin et al. |
| 2019/0282464 A1 | 9/2019 | Baldwin et al. |
| 2019/0367256 A1 | 12/2019 | Baldwin et al. |

FOREIGN PATENT DOCUMENTS

| | | |
|---|---|---|
| CA | 2886063 A1 | 4/2014 |
| CA | 2977737 C | 9/2016 |
| CA | 2982908 A1 | 10/2016 |
| CN | 1217650 A | 5/1999 |
| CN | 1713891 A | 12/2005 |
| CN | 103547247 A | 1/2014 |
| CN | 110035737 A | 7/2019 |
| DE | 10229812 A1 | 1/2004 |
| DE | 10304721 A1 | 8/2004 |
| EP | 1391192 A1 | 2/2004 |
| EP | 1508326 A1 | 2/2005 |
| EP | 2319586 A1 | 5/2011 |
| EP | 2636401 A1 | 9/2013 |
| EP | 3454662 A1 | 3/2019 |
| EP | 3454826 A1 | 3/2019 |
| EP | 3454946 A1 | 3/2019 |
| EP | 3454949 A1 | 3/2019 |
| ES | 2560540 T3 | 2/2016 |
| JP | H0625051 B2 | 2/1994 |
| WO | 0103663 A1 | 1/2001 |
| WO | 2004022019 A1 | 3/2004 |
| WO | 2005007516 A2 | 1/2005 |
| WO | 2012154918 A2 | 11/2012 |
| WO | 217112727 A1 | 6/2017 |
| WO | 2017197193 A1 | 11/2017 |
| WO | 2017197194 A1 | 11/2017 |
| WO | 2017197195 A1 | 11/2017 |
| WO | 2017197196 A1 | 11/2017 |
| WO | 2017197202 A1 | 11/2017 |

OTHER PUBLICATIONS

International Search Report and Written Opinion received in PCT/US2017/032278 dated Jul. 26, 2017, pp. 9.
International Preliminary Report received in PCT/US2017/032278 dated Nov. 13, 2018, pp. 6.
Mintel, "Hair Styling Foam", Oct. 2013, XP002772098, Online.
Mintel, "Pack Facial Mask", Mar. 2016, XP002772099, Online.
Mintel, "Body Whip Moisture Cream", Jul. 2008, XP002772100, Online.
Mintel, "Body Whip Cream", Aug. 2009, XP002772101, Online.
International Search Report and Written Opinion received in PCT/US2017/032279 dated Jul. 28, 2017, pp. 11.
International Preliminary Report received in PCT/US2017/032279 dated Nov. 13, 2018, pp. 8.
International Search Report and Written Opinion received in PCT/US2017/032281 dated Aug. 1, 2017, pp. 16.
International Preliminary Report received in PCT/US2017/032281 dated Nov. 13, 2018, pp. 11.
Canadian Office Action received in 3,023,669 dated Jul. 21, 2020, pp. 8.
Australia IP, Examination report No. 1 for standard patent application for Australian App. No. 2017263538 (dated Feb. 25, 2021).
USPTO, Non-Final Rejection of the U.S. Exam Report for U.S. Appl. No. 16/300,270 (dated Jul. 23, 2020).
CIPO, Examination Report and Examination Search Report for Canadian App. No. 3,023,714 (dated Mar. 1, 2021).
EPO, Communication pursuant to Article 94(3) EPC for European App. No. 17726753.1.
Australia IP, Examination report No. 1 for standard patent application for Australian App. No. 2017263531 (dated Feb. 25, 2021).
USPTO, Non-Final Rejection of the U.S. Exam Report on U.S. Appl. No. 16/300,289 (dated Jul. 27, 2020).
CIPO, Examination Report and Examination Search Report for Canadian App. No. 3,023,669 (dated Jan. 29, 2021).

(56) References Cited

OTHER PUBLICATIONS

Australia IP, Examination report No. 1 for standard patent application for Australian App. No. 2017263532 (dated Feb. 25, 2021).
CIPO, Examination Report and Examination Search Report for Canadian App. No. 3,023,680 (dated Feb. 17, 2021).
EPO, Communication pursuant to Article 94(3) EPC for European App. No. 17725450.5 (dated Mar. 19, 2021).
Australia IP, Examination report No. 1 for standard patent application for Australian App. No. 2017263533 (dated Feb. 25, 2021).
USPTO, Non-Final Rejection of the U.S. Exam Report on U.S. Appl. No. 16/300,323 (dated Jun. 12, 2020).
CIPO, Examination Report and Examination Search Report for Canadian App. No. 3,023,702 (dated Feb. 1, 2021).
EPO, Communication pursuant to Article 94(3) EPC for European App. No. 17726754.9 (dated Feb. 23, 2021).
Australia IP, Examination report No. 1 for standard patent application for Australian App. No. 2017263534 (dated Feb. 25, 2021).
USPTO, Non-Final Rejection of the U.S. Exam Report on U.S. Appl. No. 16/300,342 (dated Jul. 8, 2020).
CIPO, Examination Report and Examination Search Report for Canadian App. No. 3,023,703 (dated Feb. 12, 2021).
EPO, Communication pursuant to Article 94(3) EPC for European App. No. 17726162.5 (dated Apr. 2, 2021).
EPO, Communication pursuant to Article 94(3) EPC for European App. No. 17725453.9 (dated Mar. 19, 2021).
USPTO, Non-Final Rejection of the U.S. Exam Report on U.S. Appl. No. 16/300,270 (dated Feb. 5, 2021).
USPTO, Final Rejection of the U.S. Exam Report on U.S. Appl. No. 16/300,323 (dated Nov. 18, 2020).
USPTO, Final Rejection of the U.S. Exam Report on U.S. Appl. No. 16/300,342 (dated Dec. 11, 2020).
USPTO, Non-Final Rejection of the U.S. Exam Report on U.S. Appl. No. 16/300,289 (dated Feb. 5, 2021).
Mexican Patent Office, Mexican Official Action for Mexican App. No. MX/a/2018/013754 (dated Jun. 22, 2021), pp. 1-6.
USPTO, Non-Final Rejection of the U.S. Exam Report for U.S. Appl. No. 16/300,342 (dated Jun. 24, 2021), pp. 1-13.
Dailymed, "Coppertone Defend and Care Oil Free Lotion SPF 30," www.dailymed.nim.nih.gov. Published online Dec. 17, 2015, pp. 1-3.
Food Crumbles, The Science of Foams in Food, Apr. 5, 2020, https://foodcrumbles.com/science-of-foams-in-food (Year 2020), 14 pgs.
BPO, Brazilian Office Action received in Brazilian Application No. BR112018073118-8 dated Nov. 8, 2021, 4 pages.
Chinese Office Action received in Chinese Application No. 201780028415.1 dated Dec. 6, 2021, pp. 14.
Chinese Office Action received in Chinese Application No. 201780028486.1 dated Nov. 8, 2021, pp. 12.
Chinese Office Action received in 201880031248.0, dated Apr. 18, 2022, pp. 6.
USPTO, Non-Final Rejection of the U.S. Exam Report for U.S. Appl. No. 16/300,342 (dated Aug. 10, 2022).
USPTO, Final Rejection of the U.S. Exam Report on U.S. Appl. No. 16/300,342 (dated Feb. 23, 2023), 15 pages.
USPTO, Non-Final Rejection of the U.S. Exam Report on U.S. Appl. No. 16/300,323 (dated Feb. 8, 2023), 19 pages.
Second Chinese Office Action received in Chinese Application No. 201880031248.0 dated Feb. 17, 2023, pp. 4.
Cosdna, "Copperstone Kids Clear Sunscreen Lotion (SPF 50)", Nov. 24, 2016, pp. 1.
Zhang et al., "Nonionic Surfactant Application Patent Technology," China Light Industry Press, Mar. 31, 2001, pp. 1-2.
Chinese National Intellectual Property Administration, Chinese Second Office Action for App. No. 201780028415.1 (dated Sep. 5, 2022), pp. 1-17.

* cited by examiner

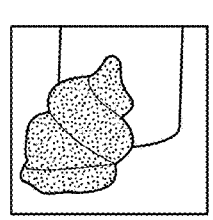
Appearance of a "Whipped-foam" delivered from a Whipped Sunscreen Lotion SPF 30

FIG. 1A

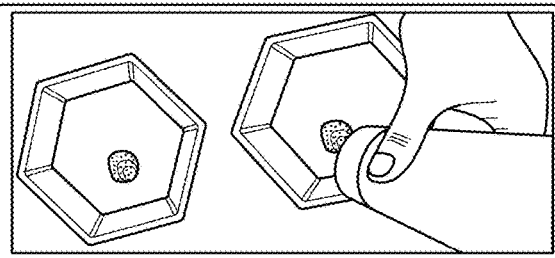
Application of Two Lotions (Left: a Whipped Sunscreen Lotion SPF 30, Right: Kiehl's Sunscreen Lotion SPF 30)

FIG. 1B-1

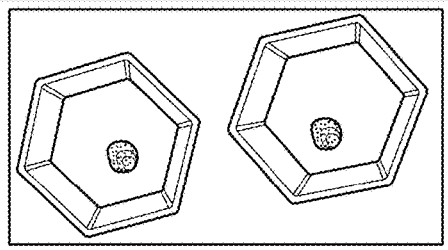
T=Initial

Applied amounts of two lotions are similar

FIG. 1B-2

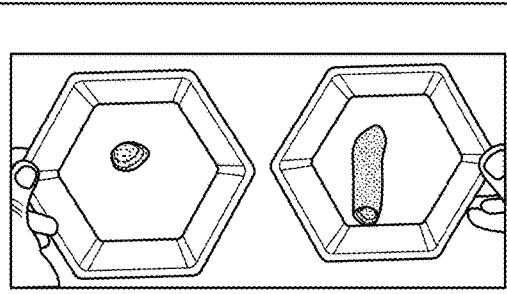
T= 10 Seconds

Left (Whipped Sunscreen SPF 30) = No change in appearance and no tendency to run
Right (Kiehl's Sunscreen SPF 30) = Become runny

FIG. 1B-3

|  | Formula Y71-098** | Y71-098 Minus Avicel | Y71-098 Minus Lanette 22 | Y71-098 Minus Avicel & Lanette 22 |
|---|---|---|---|---|
| "Whipped-foam" Dispensed at T=0* | 50°C 1 Day<br>+++ | 50°C 1 Day<br>++ | 50°C 1 Day<br>++ | 50°C 1 Day<br>- |
| "Whipped-foam" Dispensed After T=2 Min. at RT | 50°C 1 Day<br>++++ | 50°C 1 Day<br>+++ | 50°C 1 Day<br>+++ | 50°C 1 Day<br><br>50°C 1 Day<br>-<br>(After 10 seconds) |

FIG. 2

*T=0 Pictures were Taken Right After Pulling out the Samples from 50°C/75%RH Storage Condition. The Temperature of the Packaged Sample was Close to 50° C when the "Whipped-foam" was Dispensed
** CT Whipped Sunscreen Lotion SPF 50
RT: Room Temperature

|  | Formula Y71-098** | Y71-098 Minus Cetyl Alcohol | Y71-098 Minus Cetyl Alcohol & Lanette 22 | Y71-098 Minus Avicel, Lanette 22, and Ganex P-904 LC |
|---|---|---|---|---|
| "Whipped-foam" Dispensed at T=0* | +++ | +++ | ++ | -- |
| "Whipped-foam" Dispensed After T=2 Min. at RT | ++++ | +++ | ++ | -- |

FIG. 3

| | 1.2 % Behenyl Alcohol | 1.7 % Behenyl Alcohol | 2.2 % Behenyl Alcohol | 3.2 % Behenyl Alcohol | 6.2 % Behenyl Alcohol | 8.7 % Behenyl Alcohol |
|---|---|---|---|---|---|---|
| "Whipped-foam" Dispensed at T=0* | ++ | +++ | +++ | +++ | ++++ | ++++ |
| "Whipped-foam" Dispensed After 2 Min. at RT | +++ | +++ | +++ | ++++ | +++++ | +++++ |
| "Whipped-foam" Dispensed After 28 or 15 Min. at RT | N/A | ++++ (28 Min) | +++++ (15 Min) | N/A | N/A | N/A |

*T=0 Pictures were Taken Right After Pulling out the Samples from 50°C/75%RH Storage Condition. The Temperature of the Packaged Sample was Close to 50° C when the "Whipped-foam" was Dispensed
RT: Room Temperature

FIG. 4

| | Whipped After Sun Lotion Stored at RT | Whipped After Sun Lotion Stored at 50°C/75%RH for 1Day |
|---|---|---|
| "Whipped-foam" Dispensed at T=0* | [image] +++++ | [image] |
| "Whipped-foam" Dispensed After 2 Min. at RT | N/A | [image] |

*T=0 Picture for 50°C Sample was Taken Right After Pulling out the Sample from 50°C/75%RH Storage Condition. The Temperature of the Packaged Sample was Close to 50° C when the "Whipped-foam" was Dispensed   RT: Room Temperature

FIG. 5

| | | | | |
|---|---|---|---|---|
| "Whipped-foam" Dispensed After 10 Min. at RT | 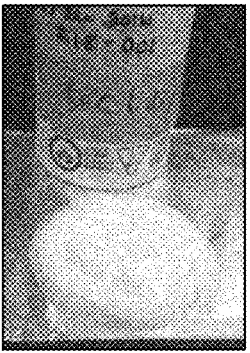<br>+++ | <br>+++ | 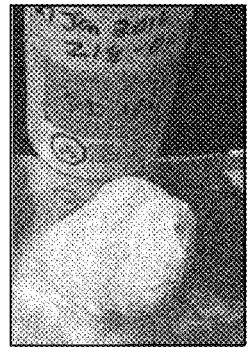<br>+++++ | N/A |
| "Whipped-foam" Dispensed After 20 Min. at RT | 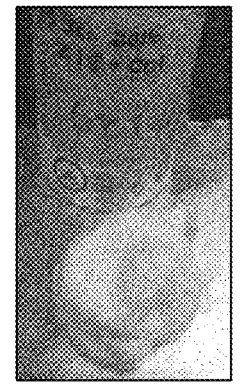<br>++++ | 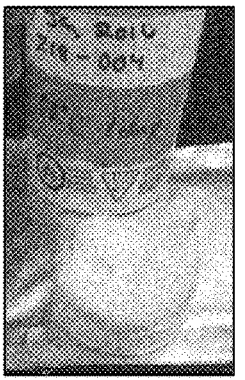<br>++++ | N/A | N/A |
*T=0 Pictures were Taken Right After Pulling out the Samples from 50°C/75%RH Storage Condition. The Temperature of the Packaged Sample was Close to 50° C when the "Whipped-foam" was Dispensed
RT: Room Temperature
FIG. 6 (Cont.)

|  | 0.5 % Behenyl Alcohol | 1.0 % Behenyl Alcohol | 5.0 % Behenyl Alcohol | 7.5 % Behenyl Alcohol |
|---|---|---|---|---|
| "Whipped-foam" Dispensed at T=0* | +++ | ++++ | +++++ | +++++ |
| "Whipped-foam" Dispensed After 2 Min. at RT | ++++ | +++++ | +++++ | N/A |
| "Whipped-foam" Dispensed After 5 or 10 Min. at RT | +++++ (10 Min) | +++++ (15 Min) | N/A | N/A |

*T=0 Pictures were Taken Right After Pulling out the Samples from 40°C/75%RH Storage Condition. The Temperature of the Packaged Sample was Close to 50° C when the "Whipped-foam" was Dispensed
RT: Room Temperature

FIG. 7

THERMAL-STABLE WHIPPED FORMULATIONS

TECHNICAL FIELD

This invention relates to the field of whipped or whippable formulations. More specifically, the invention relates to thermal-stable whipped or whippable formulations.

BACKGROUND

A formulation such as sunscreen often requires application in the sun. Sunscreen and other formulations, such as sunscreen, skincare, vitamins for oral administration, woundcare for animals or humans, whip cream, haircare, medical hair & scalp treatments, topical analgesics, skin protection, etc., may be stored at a wide temperature range. These formulations would benefit if they were thermally stable during use or storage.

SUMMARY

This disclosure provides a formulation in a package, which may be pressurized. The formulation comprises one or more active agents and one or more thermal stabilizing agents; the formulation is co-mingled (co-processed) with a first gas propellant prior to being filled under pressure into the package. The first gas propellant is added in sufficient amounts to be dispersed in the formulation.

In certain embodiments, the package maintains at least a minimal amount of pressure until substantially all the formulation in the package is expelled as a whipped formulation. In certain embodiments, the package maintains at least a minimal amount of pressure to maintain the first gas dispersed in the formulation. In certain embodiments, the pressurized package comprises a pressure generating and maintaining component. In certain embodiments, the component comprises one or more second gas and/or liquid propellant. In certain embodiments, the component is present in the package in sufficient amounts and pressure to expel the formulation as a whipped formulation upon application of external force on the formulation in the package. In certain embodiments, the amounts of the generating and maintaining component are sufficient to expel substantially all the formulation in the package as a whipped formulation. In certain embodiments, the one or more second gas and/or liquid propellant does not co-mingle with the formulation.

In other aspects, this disclosure provides a method of preparing a whippable formulation, comprising: Filling a formulation comprising one or more active agents and one or more thermal stabilizing agents; the formulation is co-mingled (co-processed) with a gas propellant under controlled temperature and under pressure into a package; wherein the gas propellant is added in sufficient amounts to be dispersed in the formulation. In certain embodiments, the pressurized package is under sufficient pressure suitable to maintain the first gas propellant dispersed in the formulation. In certain embodiments, the pressurized package is under sufficient pressure to expel the formulation as a whipped formulation upon application of external force on the formulation in the package. In certain embodiment, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more second gas and/or liquid propellant; the generating and maintaining component is present in the package in sufficient amounts and pressure to expel the formulation as a whipped formulation upon application of external force on the formulation in the package; and wherein the one or more second gas and/or liquid propellant does not co-mingle with the formulation.

In other aspects, this disclosure provides a method of using a formulation that is a whipped formulation product disclosed herein, comprising administering the formulation to a subject in need thereof.

In other aspects, this disclosure provides a package comprising the formulation disclosed herein.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 1 shows the results for appearance and stay-put-ness features: A Whipped Sunscreen Lotion SPF 30 (Finished Product: Z16-006, Concentrate: Y71-189) versus Kiehl's Lotion Activated Sun Protector™ Water-Light Lotion For Face & Body, SPF 30. FIG. 1A shows appearance of a "whipped-foam" delivered from a whipped sunscreen lotion SPF 30. FIG. 1B-1 shows application of two lotions (Left: a whipped sunscreen lotion SPF 30, Right: Kiehl's sunscreen lotion SPF 30). FIG. 1B-2 shows T=initial; Applied amounts of two lotions are similar. FIG. 1B-3 shows T=10 seconds; Left (a whipped sunscreen lotion SPF 30): no change in appearance and no tendency to run or drip (when the container is tilted); Right (Kiehl's sunscreen lotion SPF 30): became runny (when the container is tilted).

FIG. 2 shows appearance and stability of "whipped-foam" delivered from whipped sunscreen lotions containing different key functional excipients, which had been stored at 50° C./75% RH for 1 day.

FIG. 3 shows appearance and stability of "whipped-foam" delivered from whipped sunscreen lotions containing different key functional excipients, which had been stored at 50° C./75% RH for 1 day.

FIG. 4 shows appearance and stability of "whipped-foam" delivered from whipped sunscreen formulations containing different amount of behenyl alcohol, which had been stored at 50° C./75% RH for 1 day.

FIG. 5 shows appearance and stability of "whipped-foam" delivered from whipped after sun lotion stored at RT and 50° C./75% RH for 1 day.

FIG. 7 shows appearance and stability of "whipped-foam" delivered from whipped after sun formulations containing different amount of behenyl alcohol, which had been stored at 40° C./75% RH for 1 day.

DETAILED DESCRIPTION

Figure 2:
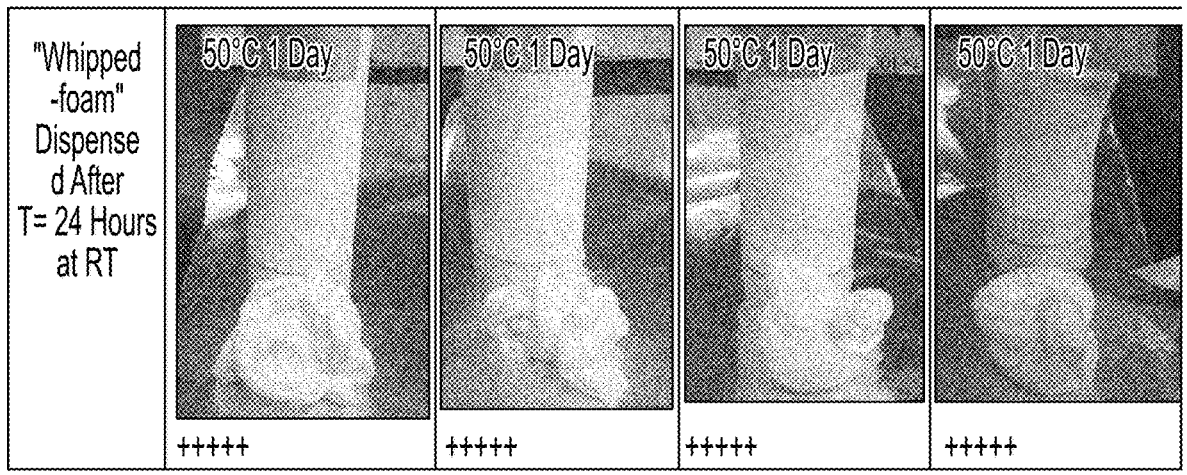

As used herein, the word "a" or "plurality" before a noun represents one or more of the particular noun. For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

This disclosure provides a formulation in a package, which may be pressurized. The formulation comprises one or more active agents and one or more thermal stabilizing agents; the formulation is co-mingled (co-processed) with a gas propellant prior to being filled under pressure (and in certain embodiments under controlled temperature) into the package. The gas propellant is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the first gas dispersed in the formulation. In certain embodiments, the pressurized package comprises a pressure generating and maintaining component. In certain embodiments, the component comprises one or more second gas and/or liquid propellant. In certain embodiments, the component is present in the package in sufficient amounts and pressure to expel the formulation as a whipped formulation upon application of external force on the formulation in the package. In certain embodiments, the amounts of the generating and maintaining component are sufficient to expel substantially all of the formulation in the package as a whipped formulation. In certain embodiments, the one or more second gas and/or liquid propellant does not co-mingle with the formulation.

The disclosed whipped formulation may be referred to herein as whipped formulation, whipped formulation product, whipped product, and the like.

In other aspects, this disclosure provides a method of preparing a whippable formulation, comprising: Filling a formulation comprising one or more active agents and one or more thermal stabilizing agents; the formulation is co-mingled (co-processed) with a gas propellant under controlled temperature and under pressure into a package; wherein the gas propellant is added in sufficient amounts to be dispersed in the formulation. In certain embodiments, the pressurized package is under sufficient pressure suitable to maintain the first gas propellant dispersed in the formulation. In certain embodiments, the pressurized package is under sufficient pressure to expel the formulation as a whipped formulation upon application of external force on the formulation in the package. In certain embodiment, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more second gas and/or liquid propellant; the generating and maintaining component is present in the package in sufficient amounts and pressure to expel the formulation as a whipped formulation upon application of external force on the formulation in the package; and the one or more second gas and/or liquid propellant does not co-mingle with the formulation.

The disclosed whipped formulation may be referred to herein as whipped formulation, whipped formulation product, whipped product, and the like.

The disclosed whippable formulation may be referred to herein as whippable formulation, whippable formulation product, whippable product, and the like.

A whipped formulation is at one time a whippable formulation.

The term "can" may be used to also mean "package."

A subject may be a human subject (user) or may be an animal subject (user). The terms "subject" and "user" are used interchangeably.

In other aspects, this disclosure provides a method of using a formulation that is a whipped formulation product disclosed herein, comprising administering the formulation to a subject in need thereof.

In other aspects, this disclosure provides a package, which may be pressurized, comprising a whippable formulation. The formulation comprises one or more active agents and one or more thermal stabilizing agents. The formulation is co-mingled (co-processed) with a gas propellant prior to being filled under pressure (and in certain embodiments under controlled temperature) into the package. In certain embodiments, the package maintains at least a minimal amount of pressure until substantially all the formulation in the package is expelled as a whipped formulation. In certain embodiments, the package maintains at least a minimal amount of pressure to maintain the first gas dispersed in the formulation. In certain embodiments, the package comprises a pressure generating and maintaining component. In certain embodiments, the component is present in the package in sufficient amounts and pressure to expel the formulation as a whipped formulation upon application of external force on the formulation in the package. In certain embodiments, the amounts of the generating and maintaining component are sufficient to expel substantially all the formulation in the package as a whipped formulation. In certain embodiments, the pressure generating and maintaining component comprises one or more second gas and/or liquid propellants which are not co-mingled with the formulation.

Whippable products include, in addition to for skincare and suncare (sunscreen and after sun care), for example and without limitation:

Category—Class—Whipped Benefit
    Whip Cream—Food—Anti-Abuse
    Peanut Butter—Food—Ease of Application
    Dessert Topping—Food—Ease of Application
    Topical Analgesic—OTC Drug—Improved Absorption
    Burn Cream—Medical Device Rx—Reduced Spreadability Pain
    Medical Haircare—Hair loss—NDA—Reduced Consumer Complaints—Failure to empty
    Medical Haircare—Scalp treatment—OTC Drug—Improved Delivery/Application
    Petrolatum Gel—OTC Drug—Ease of Application
    Hair Styling Product—Cosmetic—Novel Delivery of Thicker Products
    Diaper Rash Prevention—OTC Drug—Novel Delivery of Thicker Products
    Tooth Whitener—Cosmetic—Better Coverage Oral Care—Toothpaste—Cosmetic—Improved Delivery Anti-Fungal treatment—OTC/Rx Drug—Reduced Spread—ability Pain/Improved Absorption Eye-lid Cleanser—Cosmetic—Novel Delivery Psoriasis treatment—Medical Device—Reduced Spread—ability Pain Colon-Rectal Treatment—Rx—Improved Drug Delivery and Absorption Acne treatment—OTC Drug—Novel Delivery Hand Sanitizer—OTC Drug—Formulation Approach Natural Deodorant—Cosmetic—Improved Spread-ability Shave Prep—Cosmetic—Novel Delivery of Thicker Products Wound Care—Medical Device—Novel Delivery of Thicker Products Self-Tanner—Cosmetic—Improved Delivery Body Moisturizer—Cosmetic—Novel Delivery of Thicker Products Lice Treatment—Medical Device/OTC—Novel Delivery of Thicker Products Hair Depilatory—OTC Drug—Novel Delivery of Thicker Products Anti-Hemorrhagic—Rx/Device—Formulation Compatibility—Non-Flammability—Surgical Application.

Thus, in certain embodiments, the formulation disclosed herein comprise one or more active agents for each of the above formulations.

In certain embodiments, the whipped formulation product is a skincare product, comprising one or more skincare active agents. In certain embodiments, the whipped formulation product is a sunscreen or an after-sun product. In certain embodiments, the whipped formulation product may be an oral dosage form, such as a whipped multi-vitamin product. In certain embodiments, the whipped formulation product may be for woundcare of animals.

A subject may be a human subject (user) or may be an animal subject (user). "Subject" and "user" are used interchangeably.

In certain embodiments, the formulation further comprises a foaming agent. In certain embodiments, the formulation is for topical application.

In certain embodiments, the pressurized package in which pressure may be generated and/or maintained sufficient for the disclosed formulations is a Bag-on-valve, Piston Can, or Bag-in-Can. In other embodiments, the pressurized package is a mechanical pressure system, including for example, bladder system (such as Exxal Atomos System), which is a PowerContainer system with a rubber bladder around the outside providing pressure to the internal volume. In certain embodiments, springs are used to exert pressure on a bag. In certain other embodiments, hydrostatic pressure is used to exert pressure on a bag.

In certain embodiments, the package is a bag on valve (BOV) pressurized assembly, comprising a two-way fill/dispensing valve, an attached internal high barrier bag affixed to the valve, and rigid container adapted to and capable of holding positive pressure, affixed to the valve. In certain further embodiments, the container is glass, barrier resin, metal/alloy, or another material capable of holding positive pressure. In certain other further embodiments, the container is pre-pressurized with one or more gas and/or liquid propellants prior to filling. In certain further embodiments, the BOV pressurized assembly dispenses the whipped product in a metered dispensing system and not a continuously dosing system.

In certain embodiments, the pressurized package can comprise a "pressure generating and maintaining component," which may be a component that generates and/or maintains pressure in the package. It may refer to a chemical component or components which generate pressure, e.g., compressed gas, while inside an enclosed package, device or container (such as a can, for example). Non-limiting examples of such pressure generating and maintaining components are compressed gases/propellants and liquid propellants such as, for example, $CO_2$, propane, butane, isobutane, dimethyl ether, nitrous oxide, nitrogen, oxygen, air and the like, and suitable blends of such propellants. When a valve is opened by applying an external force, the formulation or ingredients in the device are dispensed in a 'whipped' form or a foamy form. This chemical component or components does not co-mingle with the formulation.

In certain embodiments, pre-pressurizing the package is not needed. In certain embodiments, the package is under Zero Cut Bag Pressure, where gas is present around bag but not pressurized above ambient. Filling the package at ambient pressure, the pressure inside the package would increase as the BOV expands. In certain embodiments, the package comprises an elastomeric tube/bag (akin to a tied off surgical tube). In certain further embodiments, a slight vacuum is applied. In certain embodiments, the package is pressure agnostic, in which the container cannot hold pressure around the bag. In certain embodiments, the package has Negative Cut Bag Pressure, where vacuum is present around the bag but not pressurized above ambient. Other such systems may be used, such as the Sterilflo® system (https://www.hydrasense.ca/en/why-choose-hydrasense/steriflo/).

A "skincare active agent" includes all those materials which are regarded as acceptable for use as active skin-protecting ingredients. A skincare active agent includes, for example and without limitation, skin protectant and/or anti-aging agent. Approval by a regulatory agency may sometimes be required for inclusion of active agents in formulations intended for human contact including but not limited to sunscreen active ingredients or petrolatum, white petrolatum, mineral oil, and dimethicone as skin protectants, as well as agents used as self-tanners or for diaper rash treatment and the like.

Sunscreen active agents which have been or are currently approved for sunscreen use in the United States and elsewhere include, without limitation, paraaminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, octisalate, sulisobenzone, trolamine salicylate, titanium dioxide and zinc oxide, diethanolamine methoxycinnamate, digalloyl trioleate, ethyl dihydroxypropyl PABA, glyceryl aminobenzoate, lawsone with dihydroxy acetone, red petrolatum and the like. Several other sunscreen active ingredients are accepted for use in other countries. Some non-limiting examples from outside the U.S. include Tinosorb M, Tinosorb S, Uvinul T-150, UVA sorb HEB, Uvinul A Plus, Neo Heliopan AP, Neo Heliopan MBC, and the like. It is typical to use combinations of two or more skincare active agents in a formulation. Preferably, the amount of skincare active agent or agents is present in an amount that is consistent with the FDA guidelines. The use of a combination of active agents is especially true for sunscreen formulations in order to achieve higher levels of ultraviolet absorption or to provide useful absorption over a wider range of ultraviolet wavelengths than can be the case with a single active component. Preferably, the sunscreen active agent or agents is present in an amount that is consistent with the FDA sunscreen monograph for sunscreen active agent or agents that are believed to provide the requisite SPF in accordance with the FDA monograph for such sunscreens. Other skin care active agents include sunless tanning active agents, skin protectant active agent emollients, insect repelling agents, and the like. And other agents known in the art.

After sun product is specially formulated to cool, soothe, calm, and re-hydrate (moisturize) a sunburnt or stressed skin, and to lessen the pain or itch of a sunburnt body. Currently, after sun products are available as lotion, cream, gel, or spray. The active agents in them are known in the art and any of which is within the scope of this invention. After Sun Actives are ingredients that can provide the following (but not limited) effects on skin: cooling; soothing; calming; re-hydrating (moisturizing); or relief pain/itch associated with sunburn. As an example and without limitation, an After Sun formulation contains Glycerin, Panthenol, and Aloe Barbadensis Leaf Juice to provide cool and moisturizing effects on skin. As another example, and without limitation, another After Sun formulation contains Lidocaine as an active to provide sunburn pain/itch relief.

Other active agents are contemplated. These include, for example and without limitation, sunscreen active agents, after sun active agents, vitamins, food, etc. Any active agents that can be included as a whipped formulation or a whippable formulation are within the scope of this invention. These agents are known in the art.

In certain embodiments, the thermal stabilizing agent(s) is a long chain alcohol that is 18 carbon or longer, and/or a microcrystalline cellulose based product selected from one or more product selected from a purified, partially depolymerized alpha cellulose derived from purified specialty grades of wood pulp and a product based on microcrystalline cellulose and carboxymethylcellulose sodium. In further embodiments, the long chain alcohol is behenyl alcohol. In other further embodiments, the microcrystalline cellulose based product is Avicel RC-591.

In certain embodiments, the formulation is an emulsion.

Thermal-stable whipped formulation is a formulation that remains in its whipped form after being expelled from the package after storage and/or during use at a range of temperatures.

In certain embodiments, the formulation remains stable after the formulation is expelled from the package after storage at a temperature up to about 50° C. In certain embodiments, the formulation remains stable after the formulation is expelled from the package after storage at a temperature between about −10° C. and about 50° C. In certain embodiments, the formulation remains stable after the formulation is expelled from the package after storage for at least about 1 day. In certain embodiments, the formulation remains stable after the formulation is expelled from the package after storage for at least about 2, 3, 4, 5, 6, 7, 8, 9, or 10 days, or more. In certain embodiments, the formulation remains stable after the formulation is expelled from the package after storage for at least 1 day at a temperature between about −10° C. and about 50° C.

In certain embodiments, the formulation is a sunscreen and the one or more active agents include one or more sunscreen active agents. In certain embodiments, the formulation is a sunscreen and the one or more active agents include one or more sunscreen active agents; and the formulation remains stable after storage for at least 1 day to up to one month at a temperature up to about 50° C.; the formulation comprising between about 1.2% w/w to about 8.7% w/w behenyl alcohol.

In certain embodiments, the formulation is an after sun formulation and the one or more active agents include one or more after sun active agents; and the formulation remains stable after storage for at least 1 day at a temperature up to about 50° C., wherein the formulation comprises between about 1.0% w/w to about 7.5% w/w behenyl alcohol.

In certain embodiments, the formulation is characterized by microdispersion and gas propellant level above normal saturation. In certain embodiments, the formulation is characterized by substantially consistent microvoid after the formulation is expelled from the package. In certain embodiments, the formulation is highly emollient after the formulation is expelled from the package. In certain embodiments, the formulation is readily spreadable and spreaded evenly after the formulation is expelled from the package.

In certain embodiments, the gas propellant (co-mingled or co-processed with the formulation comprising one or more active agent) is nitrogen, nitrous oxide, carbon dioxide, Argon, air or oxygen. In certain embodiments, the gas propellant in the formulation is between about 0.01% w/w to about 15.00% w/w.

In certain embodiments, the formulation has one or more of characteristics such as little or no wetness after application, having a collapse time of at least 60 seconds, or structurally stable for at least 30 minutes.

In certain embodiments, the formulation is a sunscreen and the one or more active agents include one or more sunscreen active agents.

The disclosed whipped formulation product represents the careful culmination of advancements in formulation, processing, and packaging to meet the end result of delivering a rich, creamy, spreadable, lightweight whipped product for consumer application.

Formulation:

Non-shear thickening emulsion chemistry developed to allow for high levels of gas saturation, physical stability during temperature and pressure extremes, and post-dispensing foam stability. The chemistry has also been customized to allow for the inclusion of consumer-relevant ingredients that may include, for example and without limitation, sun screen actives, moisturizers, emulsifying agents, film forming agents, thickening agents, skin feel aesthetic enhancers, antifungals, pH adjusters, pro vitamin additives, physical skin barriers, anti-bacterial agents, skin colorants, etc. Other ingredients are also contemplated, such as, without limitation, pain relief additives.

Processing:

In processing of certain embodiments, the blended formulation is transferred into a hopper, pressurized and under a controlled temperature; rate of flow and pressure is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas and formulation solution, effectively "saturating" the gas into the formulation prior to injection into the package. The gas-infused formulation is then tested for density inline and controlled under pressure and finally injected under pressure into the desired package.

The following three major steps are involved in manufacturing a whipped product (Finished Product).

1) Pre-mixing step: Co-process of a base formulation (Concentrate) and a 1st Gas.

2) Pre-pressurizing step: Pressurizing of a 2nd gas between a bag and the inside wall of the product package.

3) Packaging step: Packaging the pre-mixed formulation (concentrate+the 1st gas) into the pre-pressurized Bag on Valve (BOV) package.

Generally, a blended base formulation is transferred into a hopper, pressurized and under a controlled temperature, rate of flow and pressure is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas (1st gas) and the base formulation, effectively "dispersing" the gas into the formulation prior to injection into the pre-pressurized Bag on Valve (BOV) package. In addition, the gas-infused formulation is tested for density inline and controlled under pressure and finally injected under pressure into the desired package.

In certain embodiments, the gas propellant co-mingled with the formulation prior to filling the formulation/gas into the package is nitrous oxide gas. In certain embodiments, the Nitrous Oxide in the formulation is 0.1% w/w—4.0% w/w. In certain embodiments, the Nitrous Oxide in the formulation is about 0.1% w/w—about 10.0% w/w. In certain embodiments, the Nitrous Oxide in the formulation is about 0.1% w/w—about 1.9% w/w. In certain embodiments, the Nitrous Oxide in the formulation is about 0.1%, 1.0%, 1.9%, 2.0%, 3.0%, 4.0%, 5.0% w/w to about 6%, 7%, 8%, 9%, 10 w/w.

Nitrous Oxide has a slight sweet odor that can contribute to fragrance benefits (dual purpose gas benefits).

In certain embodiments, certain other gases can serve as a particularly good whipping agent, as evaluated by the known or estimated Ostwald Coefficients of the blended mixture and gases. Taking into consideration the potential negative effects of co-mingling of the gases with base blended formulation, example being $CO_2$, which can react with water-containing formulas to create carbonic acid and cause shifts in product pH. Alternatively, $CO_2$ can be used as a whipping gas to deliberately modify the pH of the formulation to reach targeted pH levels. Gas propellant or combinations include, without limitation, $CO_2$, argon, isobutane, nitrogen, Argon, air, oxygen, isopentane, hydrofluroolefin, other suitable gases, and combination thereof.

In certain embodiments, the gas propellant in the formulation is between about 0.01% w/w to about 15.00% w/w.

Unless otherwise noted or otherwise clear in context to a person of ordinary skill in the art, all % herein are weight to weight (w/w).

Packaging:

In certain embodiments, the pressure in the pressurized package is between about 15 psig to about 60 psig. In certain embodiments, the final pressure in the pressurized package is between about 80 psig to about 160 psig. In certain embodiments, the pressure is about 40 psig.

In certain embodiments, the package is a Bag on Valve (BOV) pressurized assembly, comprising a two way fill/dispensing valve, an attached internal high barrier bag (affixed to valve), and rigid container capable of holding positive pressure (affixed to the valve). The container may be glass, barrier resin, metal/alloy, or another material capable of holding positive pressure. The container may be "pre-pressurized" with a combination of gaseous and/or liquid propellants prior to filling, with internal pressure expected to build as the internal volume is displaced during pressurized BOV filling.

The Bag on Valve assembly and accompanying "air gap" created between bag and the pressurized rigid container help to create an insulated barrier between the formulation and the user environment. This isolative barrier is helpful to moderate the temperature swings that might be experienced when taking this product from an ambient (indoor) location to a cooler or warmer environment, such as into the sun or into vehicles located in low/high temperature environments. This barrier helps to buffer formulation temperature change and help the formulation deliver a more consistent product experience (lower temperatures can form more rigid foam structures and high temperatures can cause weaker foam structures). This feature can be particularly useful for products formulated with lower melt point foam-formers, intended for use in elevated temperature environments.

Bag on Valve delivery systems differ from traditional aerosol delivery systems in at least the following district ways: Aerosols require propellant gases to be co-joined or co-mingled into the base formulation, as would be the case in single or multiphase system. These systems use the propellant gas to both expel the product and as a foaming and/or particle breakup agent. By contrast, a Bag on Valve system includes the use of a bag within a metal can. The bag is in direct contact with the single phase formulation and is expelled by application of pressure to the outside of the bag. As such, the propellant gas inside the package never comes in contact with the product. Particle breakup or foaming can be accomplished through the dispensing actuator design and/or through the inclusion of a secondary gas within the formulation.

This BOV design has a several distinct benefits over traditional aerosol systems including without limitation:
Very high levels of product evacuation (>99% or even greater than 99.5%)
The ability to dispense formulas without the need to comingle with the propellant gas ("pure" formulation concentrate)
The ability to include gases within the formation as a foaming or particle breakup mechanism that might not serve as a sufficient propellant system
The ability to use two different gases within the system, one optimized as a propellant and one optimized as a forming or particle breakup additive.

For example, in certain embodiments, Nitrous Oxide is used as a whipping agent without allowing "free gas" to be expelled and potentially abused. By contrast, whipped cream packaging which is sold in a traditional aerosol permits the user the ability to release and potentially abuse the gas propellant/whipping agent.

The pressure generating and maintaining component may be a gas, such as gaseous propellant, a liquid, such as a liquid propellant or a blend of gas and liquid. As used herein, a gaseous propellant may also be a compressed gas, such as $CO_2$, nitrous oxide and the like. As used herein, a liquid propellant may also be a liquefied gas, such as isobutane and the like.

The pressure generating and maintaining component can be formulated inside the device in a variety of ways, depending upon the nature of the component or components that form the pressure generating and maintaining component. The vehicle, while acting as pressure-generator, may be a gas, even though it may have been packaged as, for example, a gas, a liquid or a solid. Non-limiting examples of the gas are carbon dioxide ($CO_2$), nitrous oxide ($N_2O$) and the like. Thus, for example, if the vehicle is carbon dioxide, the carbon dioxide can be 'derived' inside the sealed pressurized container in several ways. For example, the gas could be pumped into the container, or it could be added into the ingredients as "dry ice", or it could be derived or generated in situ via the chemical reaction of a suitable base with a suitable acid. In the case of "pumped in" or "dry ice", the gas is already present as $CO_2$. In the case of generation in situ via the chemical reaction of a base with an acid, the gas is generated when the acid and the base mix.

If generating the gas by chemical reaction between a base and an acid, non-limiting examples of suitable bases include sodium bicarbonate, sodium carbonate, potassium bicarbonate, potassium carbonate and the like. Non-limiting examples of suitable acids include acetic acid, citric acid and the like. Sodium bicarbonate with citric acid is a suitable combination. Because the components are being combined inside of the sealed container (device), the gas produced during the reaction is trapped which pressurizes the container.

One advantage of the inventive system is that the gas introduced or produced may be non-flammable.

In certain embodiments, the whipped formulation product is characterized by microdispersion and gas propellant level above normal saturation. In certain embodiments, the whipped formulation product is characterized by substantially consistent microvoid.

In certain embodiments, the whipped formulation product comprises at least one recognized skincare active agent.

In certain embodiments, the whipped formulation is a sunscreen formulation comprising at least one sunscreen active agent.

In certain embodiments, the whipped formulation product further comprises other ingredients, such as, for example and without limitation, one or more fatty alcohols—selected from, for example and without limitation, cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol (lanette 22), erucyl alcohol and 2-octyl-dodecanol. In certain embodiments, the whipped formulation is an after sun lotion (contains Cetyl alcohol) but optionally without any added behenyl alcohol.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In one embodiment, the disclosed whipped product formulation dispenses in a continuous stream when an external pressure is applied to the device, such as by depressing the valve/actuator, thereby eliminating the need to squeeze and shake the formulation out of a bottle or tube.

In another embodiment, the disclosed whipped product in its device (package) operates as a "one-touch" delivery system; in such system, the user will hold down the actuator until the desired amount of formulation is dispensed.

In another embodiment, the disclosed whipped product in its package offers a continuous delivery system for an application, such as, for example and without limitation, skincare applications and suncare applications. Traditionally, "continuous delivery" is typically offered as a spray product and has been very successful due to the ease and speed that it provides for sunscreen application. Many consumers, however, prefer lotions/gels over sprays and would benefit from a continuous delivery mechanism. The present invention offers such an advantage.

The disclosed whipped formulation product can be used for any application that would benefit from such product, including, for example and without limitation, skincare, sunscreen, after sun care, vitamins, woundcare, etc. For each application, the formulation needs to comprise the corresponding active agent(s) and may further comprise other appropriate ingredients.

The disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sun-screen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

The term "emulsion" identifies oil-in-water (o/w) or water-in-oil (w/o) type dispersion formulations intended for application to the skin, and air emulsion. Such dispersion formulations include, for example and without limitation, lotions and creams providing cosmetic or therapeutic benefits. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, food, vitamins, etc., depending on the intended uses for the formulations.

In certain embodiments, the whipped formulation product comprises one or more of a thickening agent and/or an emulsifying agent.

Suitable emulsifiers are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase or both, and assists with both the formation and the maintenance, or stability, of the emulsion.

Non-limiting examples of suitable emulsifiers or surfactants include pharmaceutically acceptable, non-toxic, non-ionic, anionic and/or cationic surfactants. Examples of suitable non-ionic surfactants include, for example and without limitation, glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, Prolipid and the like. An example of a suitable Prolipid is Prolipid 141 which lists behenyl alcohol, glyceryl stearate, palmitic acid, stearic acid, myristyl alcohol, lauryl alcohol, cetyl alcohol and lecithin as its ingredients in its Formula Data Sheet. Examples of suitable anionic surfactants are soaps including, for example and without limitation, alkali soaps, such as sodium, potassium and ammonium salts of aliphatic carboxylic acids, usually fatty acids, such as sodium stearate. Organic amine soaps include, for example and without limitation, organic amine salts of aliphatic carboxylic acids, usually fatty acids, such as triethanolamine stearate. Metallic soaps include salts of polyvalent metals and aliphatic carboxylic acids, usually fatty acids, such as aluminum stearate. Other classes of suitable anionic surfactants include, for example and without limitation, sulfated fatty acid alcohols such as sodium lauryl sulfate, sulfated oils such as the sulfuric ester of ricinoleic acid disodium salt, and sulfonated compounds such as alkyl sultanates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sultanate such as aryl naphthalene with alkyl substitutes. Examples of suitable cationic surfactants include, for example and without limitation, amine salts such as octadecyl ammonium chloride, quaternary ammonium compounds such as benzalkonium chloride. Non-limiting examples of emulsifiers include a mixture of cetearyl glucoside and cetearyl alcohol, available under the trade name Emulgade PL68/50 from Henkel KGaA, and PEG 30 dipolyhydroxy stearate, available under the trade name Arlacel 135 from ICI. Also preferred are various $C_{12-15}$, $C_{12-16}$ and $C_{14-15}$ alcohols available from various manufacturers, and Ceteareth 2, 10, 18, 22, Ceteth-1 and 20, cetyl dimethicone copolyol, and cetyl phosphate, glyceryl stearate, Oleth 3 and 10, polyglyceryl 3 methylglucose dis-tearate sorbitan isostearate, steareth 2, 10, and/or 20.

Other suitable emulsifiers are those known in the art for producing water-in-oil type emulsions. Non-limiting examples of some suitable water-in-oil emulsions include, for example and without limitation, SIMALINE WO (PEG-30 Dipolyhydroxystearate; available from Seppic), FLUIDANOV 20X (Octyldodecanol & Octyldodecyl Xyloside; available from Seppic), ES-5300 (Lauryl PEG-10 Tris(trimethylsiloxy)silylethyl Dimethicone; available from Dow Corning), Abil EM90 (Cetyl PEG/PPG-10/1 Dimethicone; available from Evonik) and Abil WE09 (Polyglyceryl-4 Isostearate and Cetyl PEG/PPG-10/1 Dimethicone and Hexyl Laurate; available from Evonik). The typical water-in-oil emulsifier has a HLB value of about 4 to about 6, however, this "rule" is also known to have numerous exceptions.

It may be advantageous to incorporate thickening agents, such as, for instance, Avicel RC-591,Carbopol Ultrez, Carbopol ETD 2001, available from the B. F. Goodrich Co, Abil Wax 9801, a surfactant available from Evonik, Alginic Acid, available from Kelco, cellulose gum, available from TIC Gums, ammonium acrylates copolymer, ammonium polyacryloyl dimethyl taurate, bentonite available from Southern Clay, guar hydroxypropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol, available from Nikko.

Insect repelling components are also a desirable ingredient in certain skincare and sunscreen formulations, if the formulations are to be used by persons engaged in outdoor activities. The most widely used insect repelling agent for personal care products is N,N-Diethyl-m-toluamide, frequently called "DEET" and available in the form of a concentrate containing at least about 95 percent DEET. Other synthetic chemical repellents include, for example and without limitation, dimethyl phthalate, ethyl hexanediol, indalone, di-n-propylisocinchoronate, bicycloheptene, dicarboximide, IR3535 (3-[N-Butyl-N-acetyl]-aminopropionic acid, ethyl ester; available from Merck KGaA)) and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the skincare or sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

The disclosed formulation/formulations may contain a wide range of additional, optional components. The CTFA Cosmetic Ingredient Handbook, Seventh Edition, 1997, and the Eighth Edition, 2000, which are both incorporated by reference herein in their entirety, describe a wide variety of cosmetic and pharmaceutical ingredients commonly used in skin care formulations, which are suitable for use in the formulations of the present invention. Examples of these functional classes disclosed in these references include, for example and without limitation: absorbents, abrasives, anti-caking agents, anti-foaming agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, foam boosters, hydrotropes, solubilizing agents, suspending agents (nonsurfactant), sunscreen agents, ultraviolet light absorbers, water-proofing agents, and viscosity increasing agents (aqueous and nonaqueous).

An emollient is a substance which helps to smooth and soften the skin, and may also reduce its roughness, cracking or irritation. Non-limiting examples of suitable emollients include, for example and without limitation, mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural Sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. Another suitable emollient is DC 200 Fluid 350, a silicone fluid, available from Dow Corning Corp. One or more emollients may be present ranging in amounts from about 1 percent to about 10 percent by weight, preferably about 5 percent by weight.

Other suitable emollients include, for example and without limitation, squalane, castor oil, polybutene, sweet almond oil, avocado oil, calophyllum oil, ricin oil, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and poly-alcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include, for example and without limitation, glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more of these emollients can be optionally included in the formulation.

The whipped formulations can further comprise skin protectant active agents. Suitable examples include, for example and without limitation, (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50 percent); Petrolatum (greater than 30 percent); Topical starch (10 to 98 percent); White petrolatum (greater than 30 percent); Zinc acetate (0.1 to 2 percent); Zinc carbonate (0.2 to 2 percent); and Zinc oxide (1 to 25 percent). Additional skin protectant active agents may include Colloidal oatmeal or Sodium bicarbonate.

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or formulation can range from about 15 percent to 95 weight percent.

A humectant is a moistening agent that promotes retention of water due to its hygroscopic properties. Suitable humectants include, for example and without limitation, glycerin, polymeric glycols such as poly-ethylene glycol and polypropylene glycol, mannitol and sorbitol. Preferably, the humectant is glycerin, Sorbitol 70% USP or polyethylene glycol 400, NF. More preferably, the humectant is glycerin. One or more humectants can optionally be included in the formulation in amounts from about 1 percent to about 10 percent by weight, preferably about 5 percent by weight. Other suitable humectants include, inter alia, fructose, glucose, lactic acid, PCA, potassium lactate and PCA, propylene glycol, sodium lactate and PCA.

A dry-feel modifier is an agent which when added to an emulsion, imparts a "dry feel" to the skin when the emulsion dries. Dry feel modifiers can include, for example and without limitation, talc, kaolin, chalk, starches, zinc oxide, silicone fluids, inorganic salts such as barium sulfate, surface treated silica, precipitated silica, fumed silica such as an Aerosil (silica) available from Degussa Inc., DryFlo starch (aluminum starch octenylsucinate available from Akzo Nobel), and/or an epichlorohydrin cross-linked glyceryl starch, available from Ingredion, Inc. Bridgewater, N.J., under the current tradename of Vulca 90 starch.

The disclosed formulation may additionally contain waterproofing agents. A waterproofing or water resistance agent is a hydrophobic material that imparts film forming and waterproofing characteristics to an emulsion. A waterproofing agent that can be used, for example and without limitation, is a copolymer of vinyl pyrollidone and eicosene and dodecane monomers such as the Ganex V 220, Ganex P-904 LC, and Ganex V 216 Polymers, respectively, available from Ashland Inc. Still other suitable waterproofing agents include poly alfa olefin polymers, such as Performa V 825 available from New Phase Technologies and polyanhydride resin No. 18 available under the trade name PA-18 from Chevron. Additional examples of waterproofing agents are polyurethane polymers. Some such polymers are described, for example, in U.S. Pat. No. 7,097,828.

An antimicrobial preservative may be part of the disclosed formulation. An antimicrobial preservative is a substance or preparation which destroys, prevents or inhibits the proliferation of, microorganisms in the skincare formulation, and which may also offer protection from oxidation. Preservatives are frequently used to make self-sterilizing, aqueous based products such as emulsions. This is done to prevent the development of microorganisms that may grow in the product during the manufacture and distribution of the product and/or during use by consumers, who may further inadvertently contaminate the products during normal use. Typical preservatives include, for example and without limitation, the lower alkyl esters of para-hydroxyben-zoates (parabens), especially methylparaben, propylparaben, isobutylparaben and mixtures thereof, benzyl alcohol, phenyl ethyl alcohol, benzoic acid, sodium benzoate, potassium sorbate and benzoic acid. The preferred preservative is available under the trade name of Germaben II from Sutton or a combination of chlorophenesin and benzyl alcohol. One or more antimicrobial preservatives can optionally be included in an amount ranging from about 0.001 to about 10 weight percent, preferably about 0.05 to about 1 percent.

An antioxidant may be part of the disclosed formulation. An antioxidant is a natural or synthetic substance added to the sunscreen to protect from or delay its deterioration due to the action of oxygen in the air (oxidation) and to protect the skin from sun damage. Antioxidants prevent oxidative deterioration which may lead to the generation of rancidity and nonenzymatic browning reaction products. Typical suitable antioxidants include, for example and without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringyliden-emalonate and caprylic/capric triglyceride), Vitamin A, Vitamin E and Vitamin C. One or more antioxidants can optionally be included in the formulation in an amount ranging from about 0.001 to about 5 weight percent, preferably about 0.01 to about 0.5 percent.

Chelating agents may be part of the disclosed formulation. Chelating agents are substances used to chelate or bind metallic ions, such as with a heterocyclic ring structure so that the ion is held by chemical bonds from each of the participating rings. Suitable chelating agents include, for example and without limitation, ethylene diaminetetraacetic acid (EDTA), EDTA disodium, calcium disodium edetate, EDTA trisodium, citric acid, EDTA tetrasodium and EDTA dipotassium. One or more chelating agents can optionally be included in the formulation in amounts ranging from about 0.001 to about 0.2 weight, percent preferably about 0.01% weight percent.

The disclosed formulation may include foam stabilizers or foam stabilizing agents. There are many examples of such agents and means to achieve foam stability. Non-limiting examples of suitable foam stabilizers include, for example and without limitation, the Avicels, Capmul S12L, Capmul Sl8L, Amilite GCK-12, Amadol CMA-2, Ampholak 7 CX-C, Ampholak X CO-30, Polyox WSR N-10, Amaranth S, Foam-Coll 5, Blanose 12M31XP, Genu carrageenan, Avanel S150CG and others. Avicel is an example that can be used in the formulation. For example, Avicel RC-591 is a mixture of cellulose gum and microcrystalline cellulose. Some foam stabilizers also help improve long term high temperature stability.

Fragrances are aromatic substances which can impart an aesthetically pleasing aroma to the skincare or sunscreen formulation and may be part of the disclosed formulation. Typical fragrances include, for example and without limitation, aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier may be part of the disclosed formulation. A pH modifier is a compound that will adjust the pH of a formulation to a lower, e.g., more acidic pH value, or to a higher, e.g., more basic pH value. The disclosed formulations may contain such pH modifiers as is necessary.

In an embodiment, an SPF enhancer or booster, including styrene/acrylates copolymer (such as Sunspheres PGL, commercially available from Dow Chemical), and/or skin active agents, and/or anti-oxidants, may be optionally added to the formulation.

The disclosed formulation may be used as an after-sun formulation. As used herein, an after-sun emulsion formulation is defined as a formulation that can be administered after a user has been in the sun for any amount of time and is a formulation that provides a soothing or healing effect that is pleasant to the user. Such a formulation can contain, for instance, aloe vera, vitamins A and E, cooling agents, moisturizers, redness-reducing agents and the like.

The present formulation may be used as self-tanning formulation or for sunless tanning. As used herein, the term "sunless-tanning" or "self-tanning formulations" refer to formulations which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self-tanning agent, effective amounts of a formulation coloring agent and a cosmetically acceptable carrier adapted for topical application to human skin. The self-tanning agents can also include those formulations generally accepted in the art for application to human skin, and which, when so applied, react therein with amino acids so as to form pigmented products. Such reactions give the skin a brown appearance, similar to the color obtained upon exposing it to sunlight for periods of time sufficient to tan the skin. Suitable self-tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self-tanning agents are the alpha-hydroxy aldehydes and ketones. Most preferably, the self-tanning agent is dihydroxyacetone ("DHA"). Other suitable self-tanning agents include, without limitation, methyl glyoxal, glycerol aldehyde, erythrulose, alloxan, 2,3-dihydrox-ysuccindialdehyde, 2,3-dimethoxysuccindialdehyde, 2-amino-3-hydroxy-succindialdehyde and 2-benzylamino-3-hydroxysuccindialdehyde.

The disclosed whipped formulation product has been developed, in part, to offer consumers a unique and better way to apply topical products such as sunscreen and after sun products to themselves and others.

One advantage of the disclosed whipped formulation product is during dispensing the density of the formulation contained within the package drops measurably, in one example dropping from a density roughly equal to 1.0 g/ml to 0.15-0.18 g/ml post evacuation. The resulting dispensed product represents a whipped product (a foam) of substantial rigidity and body, slow to collapse under ambient and elevated temperature conditions but easy to "break" upon physical manipulation, as for example during rubbing. This allows for a more "controlled" and even dispersal/spreading/distribution of product as compared to the initial "un-whipped" presentation of the formulation.

Another advantage of the disclosed whipped product arises from the ability to contain such a large "dispensed volume" in such a condensed package format. The volume comparison between "straight" (un-whipped) and "whipped" formulation is represented in roughly a 1:5 to 1:6 ratio, allowing for a far more consumer friendly and portable package size/format for such a large volume of dispensed product.

In certain embodiments, the disclosed whipped formulation product can allow for more control of spread over body. In certain embodiments, the disclosed whipped formulation product provides a more rigid "push" providing enhanced tactile response. In certain embodiments, the disclosed whipped formulation product is described as "thicker, creamier, and more volume," "lighter during application." In certain embodiments, the disclosed whipped formulation product allows for more control as to "heaviness" of application. In certain embodiments, the disclosed whipped formulation product provides for faster application due to perceived fast absorption.

In certain embodiments, the disclosed whipped formulation product allows for high levels of product evacuation, particularly for viscous products as compared to traditional non-pressurized emulsion packaging. In certain embodiments, the disclosed whipped formulation product with its pressured system allows for elevated levels of gas to be dispersed into formulation, beyond what ambient would normally allow, which can increase whipping potential (lower resulting dispensed densities) and reduce sputtering that can be caused by saturating high levels of gas into formulation but failing to provide adequate pressure to contain the saturated gas. In certain embodiments, the disclosed whipped formulation product results in reduced corrosion potential by separating the formulation from the rigid, pressurized container (if metal) by containing the formulation in the internal bag.

In certain embodiments, the disclosed whipped formulation product can have its gas propellant or combination, pressure, and saturation customized for each formulation. Whereas oil and water emulsions are particularly well suited for specific gases, liquid propellants can provide much larger bubble structures. BOV dispensing mechanism allows for co-blending of the various types of liquid and gas-phase propellant allowing to dispense whipped products without substantially altering temperature or potentially induce a cooling effect due to phase change energy absorption.

The disclosed whipped product is a light and spreadable formulation and thus may be particularly well suited for sensitive or compromised skin applications, such as applying a whipped sunscreen product.

The disclosed whipped product form is designed to dispense, for example and without limitation, lotion/cream/ointment/oral dosage form/whipped cream in a controlled manner by delivering a pressurized, foaming formulation via a dispensing orifice at the touch of a button. The product is dispensed via an actuator that depresses a valve stem into a female aerosol valve. Upon activation, the gas-saturated formulation experiences a drop in pressure as it moves from a pressurized containment system to ambient conditions. This change in pressure allows the saturated gas to rapidly expand, creating bubbles within the formulation, leading to a formulation of reduced density. Formulation customizations allow these bubbles to remain stable for about 10 seconds, for about 20 minutes, or longer, permitting the user to spread the resulting product onto a surface with enhanced coverage benefits.

Although specific suppliers of commercially available ingredients may be listed herein, it is understood that these products may be available from additional suppliers and that the instant invention is not limited to only that ingredient from the specifically cited supplier. Rather the supplier is being provided as an example of what is commercially available.

Description of Certain Embodiments of the Whipped Product

- Luxurious whipped product, whipped, spongy, soft, pillowy
- No shake whipping
- Not runny; stays where you put it
- Easy to apply and handle, faster, easier application
- More controllable, no drip allows precise placement, convenience of Continuous-Spray but no wet-look. Applying easily to back, not chasing a liquid product, no smear mess but pull product to control application. Can apply multiple dollops to body at one time. Thus can put package down and not have to touch again while rubbing in multiple dollops
- Quick rub-out time
- Different sensory (drag of product), smoothness
- Connect emotionally with application experience
- Perception—whipped dries more quickly
- After feel—no wetness/drag/tackiness
- Coping mechanism: whipped made convenient/quiet/easy dispose
- Characterization of the product—brightness, density, bubble size, bubble distribution, surface tension, pH, stability, sheer, dose, sound, drag (skin feel)—low drag, sheen, full bodied, insulation, contact temperature, wetness, slip, sound cue
- Change in physical properties only, maintains formulation properties with enhanced application benefits, "transforms application but not properties"
- May have 5×-10× expansion in density
- Micro-voids, micro-bubbles, infused, air emulsion, trap gas in structure
- Consistent whipped product over life of product—beginning to end
- Reduce in dead inventory
- Stable, supersaturated nitrous oxide loading, helps to create microbubbles and thus unique structure
- Can create variable drag experience based on processing reduced drag application, increased/better/easier application
- low sheer application for sensitive/damaged skin
- Create and maintain higher solubility product through containment under elevated pressure (allows constant pressure overtime)
- Size of nozzle (sheer rate impact)←sound profile One drawback of standard lotion products is their tendency to become runny or drippy after application. As shown in FIG. 1, Kiehl's sunscreen lotion, a typical sunscreen lotion product, became runny right after application. On the contrary, a whipped sunscreen lotion delivered a voluminous and creamy "whipped-foam" that does not deflate soon after dispensing, and stayed firmly on the application site and then resisted to run. This stay-put-ness attribute of whipped sunscreen products is advantageous as they do not need to be spread immediately after application.

High Sensory Impact

The disclosed whipped formulation product represents the careful culmination of advancements in formulation, processing, and packaging to deliver a rich, creamy, spreadable, lightweight whipped product for consumer application, with high sensory impact.

Sensory impact (such as appearance, sound, and skin impact) to the user may be evaluated by trained personnel to determine how product variants are perceived differently by the user, with statistical confidence. Those formulations determined to have high sensory impact are thus selected. High sensory impact is, for example, an impact to the user's senses that is greater than adequate. In certain embodiments, the user's senses are highly satisfied by the disclosed formulation after its application on the user.

Two intertwined process variables may contribute to controlling the consumer experience associated with a base formula; gas loading (e.g., Nitrous Oxide) into the formulation with the active ingredient, which impacts density, spreadability, sound, and physical appearance of product; and pre-gas can pressure, which influences stability of gas emulsion, sound, speed of dispense, sputtering, and "quality" characteristics. Multiple product variants, combining these two process variables, are run and are being physically evaluated. Physical measurements may be made, including pre-gas CT scans to yield "in can" product profile characterization details; dispensing observations (appearance, sound, etc.) and high temperature foam stability; and post-dispensing physical measurements including density, bubble size, and bubble size distribution. Sensory impact (such as appearance, sound, and skin impact) to the user of these multiple product variants may be evaluated by trained personnel to determine how product variants are perceived differently by the user, with statistical confidence. Some of these tested whipped formulations would have high sensory impact to the user. For any given product, the following parameters, as well as any other parameters that impact a user's sense(s), may be evaluated.

Appearance: visual compactness, integrity of shape, gloss, hue, intensity, brightness, opacity, whitening.

Sound: volume, tone, crackling/popping, sputtering. Skin Feel: firmness, stickiness, cohesiveness, peaking, wetness, spread-ability, coolness, thickness, slipperiness, oiliness, waxiness, greasiness, rubs to absorbency, tautness, roughness, thickness of residue, grittiness, graininess, chalkiness, peeling/flaking, pilling, powdery-ness, plastic/coated.

In certain embodiments, the whipped formulations have high sensory impact to a user, who may be a human user. These formulations with high sensory impact are characterized by one or more of the following: positive appearance, low sound impact, high integrity of shape, visual compactness, high spreadability, positive skin feel, afterfeel (immediately after application or after a few minutes after application, such as about 10 minutes after) as well as other sensory input perceivable by a user.

In certain embodiments, the disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sunscreen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In certain embodiments, the disclosed formulation has one or more of the following physical characteristics: a majority of bubbles being of a bubble size of less than 20 µm, mean number of bubbles of about less than 20%, and high foam stability. In certain embodiments, the disclosed formulations have high foam stability at high temperatures, such as at 25° C. to 37° C., or 37° C. to 50° C.

In certain embodiments, the color of the whipped formulation post-dispensing is white. The whiteness of the whipped lotion may be used as a visual queue for application on skin.

In certain embodiments, the formulation has at least about 60% of the gas bubbles at ≤100 µm, after the formulation is expelled from the package. In certain embodiments, the formulation has at least about 40% of the gas bubbles at ≤60 µm, after the formulation is expelled from the package.

In certain embodiments, the whipped formulation product is characterized by microdispersion. In certain embodiments, the whipped formulation product is characterized by substantially consistent microvoid.

In certain embodiments, the whipped formulation product is highly emollient. In certain embodiments, the whipped formulation product has about 60% or more of the gas bubbles at ≤100 µm. In certain other embodiments, the whipped formulation product has about 40% or more of the gas bubbles at ≤60 µm. The gas bubbles are formed from the gas propellant co-mingled with the formulation prior to filling the formulation into the package.

In certain embodiments, the formulation has one or more of characteristics such as little or no wetness after application, having a collapse time of at least 60 seconds, or structurally stable for at least 30 minutes.

EXAMPLES

For this invention to be better understood, the following examples are set forth. These examples are for purposes of illustration only and are not be construed as limiting the scope of the invention in any manner.

Example 1. Evaluating Factors for Thermal-Stable Formulations

A new "whipped" platform technology has been successfully applied for developing Sunscreen and After Sun products, and is being utilized in developing various products including medicated dermal products. These whipped products (Finished Product) consists of a base emulsion formulation (Concentrate) and a propellant (Gas), which is then packaged into a pre-pressurized Bag on Valve (BOV) package.

The objective of this study is to evaluate the effect of key functional ingredients on the performance of whipped products. For this evaluation, the appearance of "whipped-foam" ucts dispensed from whipped products has been graded from a stable, creamy, and fully whipped (+++++) to a liquid form (−). The following general description captures the appearance of the "whipped-foam" corresponding to each of the grades observed.

a. +++++: stable, rich creamy appearance, and fully whipped foam
b. ++++: the "whipped-foam" largely maintains its appearance and structure/shape
c. +++: the "whipped-foam" lost some of its appearance and structure/shape
d. ++: the "whipped-foam" lost much of its appearance and structure/shape
e. +: the "whipped-foam" lost most of its appearance and structure/shape
f. −: the "whipped-foam" lost its appearance and structure/shape completely and is in viscous liquid form
g. −−: the "whipped-foam" lost its appearance and structure/shape completely and is in runny liquid form The present studies are focused on evaluating key functional ingredients which can control and improve effectively the performance of whipped products, particularly the stability of their dispensed "whipped-foams". Formulations from each Sunscreen and After Sun product categories were selected as model formulations to investigate the effect of key functional ingredients on the performance of whipped products.

All tested formulations are manufactured and packaged at Memphis R&D laboratory (brief manufacturing process is provided in Appendices A and B). In general, a whipped product (Finished Product) should be prepared by 1) pre-mixing step: co-process of a base formulation (Concentrate) and a 1st Gas, 2) pre-pressurizing step: pressurizing of a 2nd gas between a bag and the inside wall of the product can, and 3) packaging step: packaging the pre-mixed formulation (concentrate +the 1st gas) into the pre-pressurized Bag on Valve (BOV) package. For this study, a pre-pressurized BOV package and the pre-mixing step were not utilized. However, in order to mimic the performance of a typical whipped product, the mixture of a base formulation and nitrous oxide in a package was shaken vigorously before dispensing. In addition, a careful dispensing method was utilized to meet the end result of delivering a rich, creamy, spreadable, lightweight "whipped-foam". Formulation details for whipped Sunscreen and After Sun products used in the following evaluation studies are summarized in Tables 1 and 2.

Evaluation Study I: Investigation of Key Functional Ingredients in Whipped Products The effects of key functional ingredients on whipped products stored at 50° C./75% RH for 1 day are tested. The high temperature condition is used to visualize and differentiate each functional ingredient's effect on the whipped products.

As shown in FIG. 2, both Lanette 22 (Behenyl alcohol) and Avicel RC-591 have great impact on the high temperature stability of the whipped products. The "whipped-foam" delivered from the control formulation (Y71-098), which contains both Lanette 22 and Avicel, appears slightly lost some of its appearance and structure at T=0 (right after storage at 50° C./75% RH for 1 day, the temperature of the packaged sample is close to 50° C. when the 'whipped-foam" was dispensed). However, even after staying at RT for 2 minutes, the control formulation is able to deliver "whipped-foam" that largely maintains its appearance and structure. The effects of Lanette 22 and Avicel on the high temperature stability of whipped formulations are comparable. As expected, the "whipped-foam" delivered from the formulation without both Avicel and Lanette 22 losing its appearance and structure completely and becomes a viscous liquid at both T=0 and T=2 minutes at RT.

Figure 3:
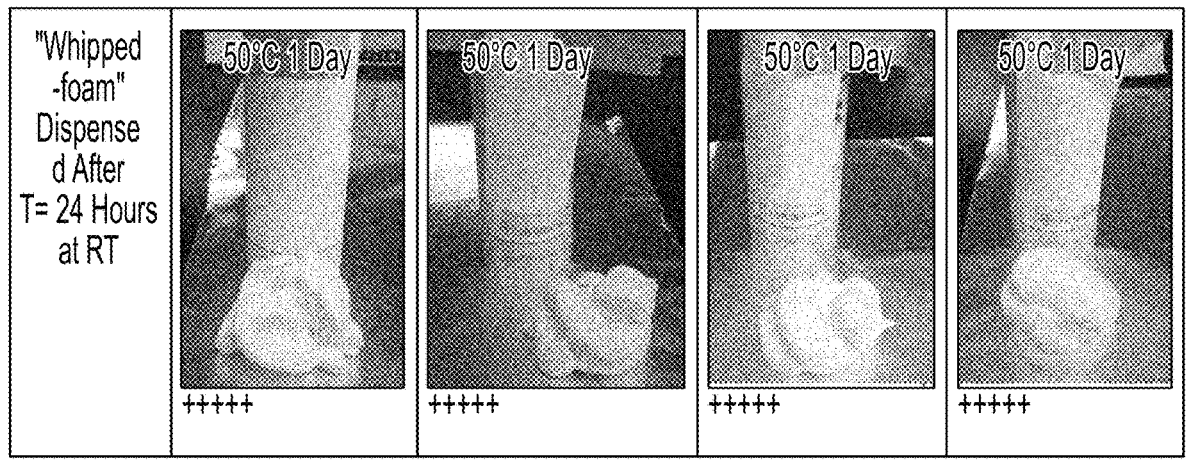

Neither cetyl alcohol ($C_{16}$ fatty alcohol) nor Ganex P-904 LC (a film former that provides water and wears resistance) appears to improve the thermal stability of the whipped products substantially (FIG. 3). The results in FIGS. 2 and 3 also demonstrate that regardless of heat stress, all tested formulations are able to deliver stable "whipped-foams" after remaining at room temperature (RT) for 24 hours.

Based on these results, the order of "whipped-foam" dispensed is as follows.

At T=0,

The control (+++)>the control minus Cetyl alcohol (+++)>the control minus Avicel (++)=the control minus Lanette 22 (++)=the control minus both Cetyl alcohol and Lanette 22 (++)>the control minus both Avicel and Lanette 22 (−)>the control minus Avicel, Ganex P-904, and Lanette 22 (−−).

At T=2 minutes at RT,

The control (++++)>the control minus Cetyl alcohol (+++)=the control minus Avicel (+++)=the control minus Lanette 22 (+++)>the control minus both Cetyl alcohol and Lanette 22 (++)>the control minus both Avicel and Lanette 22 (−)>the control minus Avicel, Ganex P-904, and Lanette 22 (−−).

Evaluation Study II: The Effect of varying Behenyl Alcohol Amount on the Stability of Whipped Sunscreen Products Whipped sunscreen formulations with behenyl alcohol concentration ranging from 1.2% w/w to 8.7% w/w are prepared and evaluated for their stability at the high temperature (50° C./75% RH for 1 day). Each whipped lotion formulation contains 4.50% w/w Prolipid 141. Table 3 lists the concentration for each of the ingredients in the prolipid 141 per each whipped lotion formulation.

As presented in FIG. 4, increasing the concentration of behenyl alcohol from 1.2% w/w to 6.2% w/w significantly improves the stability of the whipped formulations for 50° C. storage. Maximum improvement is achieved by the formulation containing 6.2% w/w behenyl alcohol. The effect of increasing the concentration of behenyl alcohol from 6.2% w/w to 8.7% w/w on the stability of the whipped formulations is negligible. The score of "whipped-foam" from whipped sunscreen formulations containing different amount of behenyl alcohol (BA) is as follows.

At T=0, 1.2% BA (++)<1.7% BA (+++)<2.2% BA (+++)=3.2% BA (+++)<6.2% BA (++++)=8.7% BA (++++)

At T=2 minutes at RT, 1.2% BA (+++)=1.7% BA (+++)=2.2% BA (+++)<3.2% BA (++++)<6.2% BA (+++++)=8.7% BA (+++++)

At T=28 minutes at RT, 1.7% BA (++++)<2.2% BA (+++++)

Evaluation Study III: The Effect of Varying Behenyl Alcohol Amount on the Stability of Whipped after Sun Products Similarly to whipped sunscreen products, a whipped after sun lotion also delivers a voluminous and creamy "whipped-foam" at RT. When stored at 50° C./75% RH for 1 day, the "whipped-foam" delivered from whipped after sun lotion losts its appearance and structure completely and becomes a runny liquid even after staying at RT for 2 minutes (FIG. 5). In order to investigate whether different levels of behenyl alcohol (Lanette 22) can provide adequate whipped after sun lotion stability at elevated temperature, after sun formulations containing various concentration of behenyl alcohol are prepared and stored at two different storage conditions (1 day at 40° C./20% RH and 1 day at 50° C./75% RH).

Figure 6:
FIG. 6 shows appearance and stability of "whipped-foam" delivered from whipped after sun formulations containing different amount of behenyl alcohol, which had been stored at 50° C./75% RH for 1 day.

It is readily seen that the stability of the whipped after sun formulations at 50° C. improves markedly when the concentration of behenyl alcohol rose from 1.0% w/w to 7.5% w/w (FIG. 6). Maximum improvement is achieved by the formulation containing 7.5% w/w behenyl alcohol. The minimum concentration of behenyl alcohol required to maintain the adequate "whipped-foam" stability at the high temperature (at 50° C.) needs to be >1.0% w/w. No enhancement of "whipped-foam" stability was observed when behenyl alcohol concentration is increased from 0.5% w/w to 1.0% w/w. The score of "whipped-foam" from whipped after sun formulations containing different amount of behenyl alcohol (BA) after 1 day at 50° C./75% RH is as follows.

At T=0, 0% BA (−−)=0.5% BA (−−)=1.0% BA (−−)<5.0% BA (++++)<7.5% BA (+++++)

At T=2 minutes at RT,

0% BA (−−)<0.5% BA (−)=1.0% BA (−)<5.0% BA (++++)

At T=10 minutes at RT, 0.5% BA (+++)=1.0% BA (+++)<5.0% BA (+++++)

At T=20 minutes at RT, 0.5% BA (++++)=1.0% BA (++++)

For samples stored at 40° C., at T=0, the presence of behenyl alcohol (from 0.5% to 5.0%) improves the stability of whipped after sun formulations, but increasing the behenyl alcohol content from 5.0% to 7.5% has no impact (FIG. 7). The score of "whipped-foam" from whipped after sun formulations containing different amount of behenyl alcohol (BA) after 1 day at 40° C./75% RH is as follows.

At T=0, 0.5% BA (+++)<1.0% BA (++++)<5.0% BA (+++++)=7.5% BA (+++++)

At T=2 minutes at RT, 0.5% BA (++++)<1.0% BA (+++++)

At T=10 minutes at RT, 0.5% BA (+++++)

The results in FIGS. 2-7 clearly demonstrate the impact of behenyl alcohol and or Avicel on the temperature stability of whipped sunscreen and after sun formulations.

In Summary, the effect of key functional ingredients on the performance of whipped products is evaluated. Among tested key ingredients, Avicel and Lanette 22 (behenyl alcohol) are found to be highly effective in terms of improving the stability of the whipped products at higher temperature. Cetyl alcohol and Ganex P-904 do not appear to contribute to this improvement. Therefore, adding Lanette 22 and/or Avicel into whipped formulations helps them maintain the desired product experience when used after high temperature exposure.

Moreover, increasing the concentration of behenyl alcohol significantly improves the stability of the whipped sunscreen and after sun formulations, indicating that incorporating behenyl alcohol into formulations is an effective way to enhance the temperature stability of the whipped formulations.

TABLE 1

Formula Comparison of Whipped Sunscreen Products Used in Evaluation Studies

Table 1.A: Composition of Whipped Sunscreen Products (Finished Products)

| Component | Concentration (% w/w) | | | | | | | | | | |
|---|---|---|---|---|---|---|---|---|---|---|---|
| | Z16-016 (SPF 50) | Z16-016 minus Avicel | Z16-016 minus Lanette 22 | Z16-016 minus Avicel & Lanette 22 | Z16-016 minus Cetyl alcohol | Z16-016 minus Cetyl alcohol and Lanette 22 | Z16-016 minus Avicel, Cetyl alcohol and Lanette 22 | 1.7% behenyl alcohol | 2.2% behenyl alcohol | 6.2% Behenyl alcohol | 8.7% behenyl alcohol |
| Whipped Sunscreen Lotion Concentrate SPF 50 (Y71-098) | 98.10 | — | — | — | — | — | — | — | — | — | — |
| Whipped Sunscreen Lotion Concentrate (Z16-104) | — | 98.10 | — | — | — | — | — | — | — | — | — |
| Whipped Sunscreen Lotion Concentrate (Z16-100) | — | — | 98.10 | — | — | — | — | — | — | — | — |
| Whipped Sunscreen Lotion Concentrate (Z16-123) | — | — | — | 98.10 | — | — | — | — | — | — | — |
| Whipped Sunscreen Lotion Concentrate (Z16-137) | — | — | — | — | 98.10 | — | — | — | — | — | — |
| Whipped Sunscreen Lotion Concentrate (Z16-141) | — | — | — | — | — | 98.10 | — | — | — | — | — |
| Whipped Sunscreen Lotion Concentrate (Z16-126) | — | — | — | — | — | — | 98.10 | — | 41- | — | — |
| Whipped Sunscreen Lotion Concentrate (Z16-184) | — | — | — | — | — | — | — | 98.10 | — | — | — |
| Whipped Sunscreen Lotion Concentrate (Z16-158) | — | — | — | — | — | — | — | — | 98.10 | — | — |
| Whipped Sunscreen Lotion Concentrate (Z16-162) | — | — | — | — | — | — | — | — | — | 98.10 | — |
| Whipped Sunscreen Lotion Concentrate (Z16-180) | — | — | — | — | — | — | — | — | — | — | 98.10 |
| Nitrous Oxide | 1.90 | 1.90 | 1.90 | 1.90 | 1.90 | 1.90 | 1.90 | 1.90 | 1.90 | 1.90 | 1.90 |

TABLE 1-continued

Formula Comparison of Whipped Sunscreen Products Used in Evaluation Studies

Table 1.B: Ingredient Composition of Whipped Sunscreen Concentrates SPF 50 (Base Formulas)

| Ingredient | INCI Name | Function | Concentration (% w/w) | | | |
| --- | --- | --- | --- | --- | --- | --- |
| | | | Y71-098 | Z16-100 | Z16-104 | Z16-123 |
| Avicel RC-591 | Microcrystalline Cellulose (&) Cellulose Gum | Thickening agent | 2.00 | 2.00 | — | — |
| Disodium EDTA | Disodium EDTA | Chelating agent | 0.10 | 0.10 | 0.10 | 0.10 |
| Ganex P-904 LC | Butylated PVP | Film former | 0.80 | 0.80 | 0.80 | 0.80 |
| Glycerin | Glycerin | moisturizer | 2.50 | 2.50 | 2.50 | 2.50 |
| Sunspheres PGL | Styrene/Acrylates Copolymer (+) Water | SPF booster | 8.00 | 8.00 | 8.00 | 8.00 |
| Octocrylene | Octocrylene | Active | 4.00 | 8.00 | 8.00 | 8.00 |
| Octisalate, USP | Ethylhexyl Salicylate | Active | 4.50 | 4.50 | 4.50 | 4.50 |
| Homosalate | Homosalate | Active | 10.00 | 10.00 | 10.00 | 10.00 |
| Dicaprylyl Ether | Dicaprylyl Ether | | 2.00 | 2.00 | 2.00 | 2.00 |
| Tocopherol | Tocopherol (Vitamin E) | antioxidant | 0.25 | 0.25 | 0.25 | 0.25 |
| Avobenzone | Butyl Methoxydibenzoylmethane | Active | 3.00 | 3.00 | 3.00 | 3.00 |
| Oxybenzone | Benzophenone-3 | Active | 6.00 | 6.00 | 6.00 | 6.00 |
| Prolipid 141 | Behenyl Alcohol, Glyceryl Stearate, Palmitic Acid, Stearic Acid, Myristyl Alcohol, Lauryl Alcohol, Cetyl Alcohol, Lecithin. | Gel former, moisturizer | 4.50 | 4.50 | 4.50 | 4.50 |
| Lanette 22 (CM) | Behenyl Alcohol | Viscosity regulator | 2.00 | — | 2.00 | — |
| Cetyl Alcohol | Cetyl Alcohol | lubricant, thickener | 1.00 | 1.00 | 1.00 | 1.00 |
| Chlorphenesin | Chlorphenesin | preservative | 0.27 | 0.27 | 0.27 | 0.27 |
| Sodium Ascorbyl Phosphate | Sodium Ascorbyl Phosphate | antioxidant | 0.01 | 0.01 | 0.01 | 0.01 |
| Benzyl Alcohol | Benzyl Alcohol | preservative | 0.90 | 0.90 | 0.90 | 0.90 |
| Dry-Flo Pure | Aluminum Starch | Skin feel modifier | 4.00 | 4.00 | 4.00 | 4.00 |
| Water | Water | Solvent | Q.S. | Q.S. | Q.S. | Q.S. |

Table 1.C: Ingredient Composition of Whipped Sunscreen Concentrates SPF 50 (Base Formulas)

| Ingredient | INCI Name | Function | Concentration (% w/w) | | |
| --- | --- | --- | --- | --- | --- |
| | | | Z16-126 | Z16-137 | Z16-141 |
| Avicel RC-591 | Microcrystalline Cellulose (&) Cellulose Gum | Thickening agent | — | 2.00 | 2.00 |
| Disodium EDTA | Disodium EDTA | Chelating agent | 0.10 | 0.10 | 0.10 |
| Ganex P-904 LC | Butylated PVP | Film former | — | 0.80 | 0.80 |
| Glycerin | Glycerin | moisturizer | 2.50 | 2.50 | 2.50 |
| Sunspheres PGL | Styrene/Acrylates Copolymer (+) Water | SPF booster | 8.00 | 8.00 | 8.00 |
| Octocrylene | Octocrylene | Active | 4.00 | 8.00 | 8.00 |
| Octisalate, USP | Ethylhexyl Salicylate | Active | 4.50 | 4.50 | 4.50 |
| Homosalate | Homosalate | Active | 10.00 | 10.00 | 10.00 |
| Dicaprylyl Ether | Dicaprylyl Ether | | 2.00 | 2.00 | 2.00 |
| Tocopherol | Tocopherol (Vitamin E) | antioxidant | 0.25 | 0.25 | 0.25 |
| Avobenzone | Butyl Methoxydibenzoylmethane | Active | 3.00 | 3.00 | 3.00 |
| Oxybenzone | Benzophenone-3 | Active | 6.00 | 6.00 | 6.00 |
| Prolipid 141 | Behenyl Alcohol, Glyceryl Stearate, Palmitic Acid, Stearic Acid, Myristyl Alcohol, Lauryl Alcohol, Cetyl Alcohol, Lecithin. | Gel former, moisturizer | 4.50 | 4.50 | 4.50 |

TABLE 1-continued

Formula Comparison of Whipped Sunscreen Products Used in Evaluation Studies

| Ingredient | INCI Name | Function | | | |
|---|---|---|---|---|---|
| Lanette 22 (CM) | Behenyl Alcohol | Viscosity regulator | — | 2.00 | — |
| Cetyl Alcohol | Cetyl Alcohol | lubricant, thickener | 1.00 | — | — |
| Chlorphenesin | Chlorphenesin | preservative | 0.27 | 0.27 | 0.27 |
| Sodium Ascorbyl Phosphate | Sodium Ascorbyl Phosphate | antioxidant | 0.01 | 0.01 | 0.01 |
| Benzyl Alcohol | Benzyl Alcohol | preservative | 0.90 | 0.90 | 0.90 |
| Dry-Flo Pure | Aluminum Starch | Skin feel modifier | 4.00 | 4.00 | 4.00 |
| Water | Water | Solvent | Q.S. | Q.S. | Q.S. |

Table 1.D: Ingredient Composition of Whipped Sunscreen Concentrates SPF 50 (Base Formulas)

| | | | Concentration (% w/w) | | | |
|---|---|---|---|---|---|---|
| Ingredient | INCI Name | Function | Z16-184 | Z16-158 | Z16-162 | Z16-180 |
| Avicel RC-591 | Microcrystalline Cellulose (&) Cellulose Gum | Thickening agent | 2.00 | 2.00 | 2.00 | 2.00 |
| Disodium EDTA | Disodium EDTA | Chelating agent | 0.10 | 0.10 | 0.10 | 0.10 |
| Ganex P-904 LC | Butylated PVP | Film former | 0.80 | 0.80 | 0.80 | 0.80 |
| Glycerin | Glycerin | moisturizer | 2.50 | 2.50 | 2.50 | 2.50 |
| Sunspheres PGL | Styrene/Acrylates Copolymer (+) Water | SPF booster | 8.00 | 8.00 | 8.00 | 8.00 |
| Octocrylene | Octocrylene | Active | 4.00 | 8.00 | 8.00 | 8.00 |
| Octisalate, USP | Ethylhexyl Salicylate | Active | 4.50 | 4.50 | 4.50 | 4.50 |
| Homosalate | Homosalate | Active | 10.00 | 10.00 | 10.00 | 10.00 |
| Dicaprylyl Ether | Dicaprylyl Ether | | 2.00 | 2.00 | 2.00 | 2.00 |
| Tocopherol | Tocopherol (Vitamin E) | antioxidant | 0.25 | 0.25 | 0.25 | 0.25 |
| Avobenzone | Butyl Methoxydibenzoylmethane | Active | 3.00 | 3.00 | 3.00 | 3.00 |
| Oxybenzone | Benzophenone-3 | Active | 6.00 | 6.00 | 6.00 | 6.00 |
| Prolipid 141 | Behenyl Alcohol, Glyceryl Stearate, Palmitic Acid, Stearic Acid, Myristyl Alcohol, Lauryl Alcohol, Cetyl Alcohol, Lecithin. | Gel former, moisturizer | 4.50 | 4.50 | 4.50 | 4.50 |
| Lanette 22 (CM) | Behenyl Alcohol | Viscosity regulator | 0.50 | 1.00 | 5.00 | 7.50 |
| Cetyl Alcohol | Cetyl Alcohol | lubricant, thickener | 1.00 | 1.00 | 1.00 | 1.00 |
| Chlorphenesin | Chlorphenesin | preservative | 0.27 | 0.27 | 0.27 | 0.27 |
| Sodium Ascorbyl Phosphate | Sodium Ascorbyl Phosphate | antioxidant | 0.01 | 0.01 | 0.01 | 0.01 |
| Benzyl Alcohol | Benzyl Alcohol | preservative | 0.90 | 0.90 | 0.90 | 0.90 |
| Dry-Flo Pure | Aluminum Starch | Skin feel modifier | 4.00 | 4.00 | 4.00 | 4.00 |
| Water | Water | Solvent | Q.S. | Q.S. | Q.S. | Q.S. |

TABLE 2

Formula Comparison of Whipped After Sun Products Used in Evaluation Studies

Table 2.A: Composition of Whipped After Sun Products (Finished Products)

| | Concentration (% w/w) | | | | |
|---|---|---|---|---|---|
| Component | Z16-023 | Z16-023 + 0.5% behenyl alcohol | Z16-023 + 1.0% behenyl alcohol | Z16-023 + 5.0% behenyl alcohol | Z16-023 + 7.5% behenyl alcohol |
| Whipped After Sun Lotion Concentrate (Z16-020) | 98.10 | — | — | — | — |

TABLE 2-continued

Formula Comparison of Whipped After Sun Products Used in Evaluation Studies

| | | | | | |
|---|---|---|---|---|---|
| Whipped After Sun Lotion Concentrate (Z18-001) | — | 98.10 | — | — | — |
| Whipped After Sun Lotion Concentrate (Z18-004) | — | — | 98.10 | — | — |
| Whipped After Sun Lotion Concentrate (Z18-007) | — | — | — | 98.10 | — |
| Whipped After Sun Lotion Concentrate (Z18-010) | — | — | — | — | 98.10 |
| Nitrous Oxide | 1.90 | 1.90 | 1.90 | 1.90 | 1.90 |

Table 2.B: Ingredient Composition of Whipped After Sun Concentrates (Base Formulas)

| | | | Concentration (% w/w) | | | | |
|---|---|---|---|---|---|---|---|
| Ingredient | INCI Name | Function | Z16-020 | Z18-001 | Z18-004 | Z18-007 | Z18-010 |
| Promulgen G | Stearyl Alcohol & Ceteareth-20 | emulsifier | 4.00 | 4.00 | 4.00 | 4.00 | 4.00 |
| TegoCare 165 (formerly Lipomulse 165) | Glyceryl Stearate (&) PEG-100 Stearate | emulsifier | 3.00 | 3.00 | 3.00 | 3.00 | 3.00 |
| Dimethicone, NF 350 cst | Dimethicone | lubricant | 0.50 | 0.50 | 0.50 | 0.50 | 0.50 |
| Glycerin | Glycerin | moisturizer | 3.00 | 3.00 | 3.00 | 3.00 | 3.00 |
| Oxynex ST Liquid | Diethylhexyl Syringylidenemalonate (&) Caprylic/Capric Triglyceride | protects light-sensitive ingredients | 0.50 | 0.50 | 0.50 | 0.50 | 0.50 |
| Actiplex 5224 Lipo M (# 405224-17) | * | Botanical extracts | 0.10 | 0.10 | 0.10 | 0.10 | 0.10 |
| Permethyl 101A | Isohexadecane | emollient | 5.00 | 5.00 | 5.00 | 5.00 | 5.00 |
| Isopropyl Palmitate | Isopropyl Palmitate | emollient | 5.00 | 5.00 | 5.00 | 5.00 | 5.00 |
| DL-Panthenol 50L | Panthenol (Pro-Vitamin B5) (&) Water | moisturizer | 0.10 | 0.10 | 0.10 | 0.10 | 0.10 |
| Vitamin E | Vitamin E | antioxidant | 0.50 | 0.50 | 0.50 | 0.50 | 0.50 |
| Aloe Vera Gel 40:1 | Aloe Barbadensis Leaf Juice | Moisturizer/ antioxidant | 0.375 | 0.375 | 0.375 | 0.375 | 0.375 |
| Lanette 22 (CM) | Behenyl Alcohol | Viscosity regulator | — | 0.50 | 1.00 | 5.00 | 7.50 |
| Cetyl Alcohol | Cetyl Alcohol | lubricant, thickener | 2.00 | 2.00 | 2.00 | 2.00 | 2.00 |
| Chlorphenesin | Chlorphenesin | preservative | 0.20 | 0.20 | 0.20 | 0.20 | 0.20 |
| Benzyl Alcohol | Benzyl Alcohol | preservative | 0.70 | 0.70 | 0.70 | 0.70 | 0.70 |
| Fragrance, Mango SZ-1010 Mod | Fragrance | Fragrance | 0.20 | 0.20 | 0.20 | 0.20 | 0.20 |
| Water | Water | Solvent | Q.S. | Q.S. | Q.S. | Q.S. | Q.S. |

Mineral Oil (and)
*Theobroma Cacao* (Cocoa) Seed Butter (and)
*Prunus Armeniaca* (Apricot) Fruit Extract (and)
*Chamomilla Recutita* (*Matricaria*) Flower, Extract (and)
*Eucalyptus Globulus* Leaf Extract (and)
*Mangifera Indica* (Mango) Fruit Extract (and)
*Carica Papaya* (Papaya) Fruit Extract (and)
* *Aloe Barbadensis* Leaf Extract Each whipped lotion formulation contains 4.50% w/w Prolipid 141.

Table 3 lists the concentration for each of the ingredients in the prolipid 141 per each whipped lotion formulaton

TABLE 3

| Ingredients in the prolipid 141 | Concentration (% w/w) |
| --- | --- |
| Behenyl Alcohol | 1.215 |
| Glyceryl Stearate | 1.215 |
| Palmitic Acid | 0.72 |
| Stearic Acid | 0.63 |
| Myristyl Alcohol | 0.36 |
| Lauryl Alcohol | 0.09 |
| Cetyl Alcohol | 0.09 |
| Lecithin | 0.18 |

Appendix A. Laboratory manufacturing process for Whipped Sunscreen Lotion SPF 50 (Finished Product: Z16-016, Concentrate: Y71-098)

1. Concentrate (Base Formulation): Whipped Sunscreen Lotion Concentrate (Y71-098), Batch Size: 1000 g

TABLE 4

| | Concentration (% w/w) | Manufacturing Directions |
| --- | --- | --- |
| Part A Ingredients | | |
| Purified water, USP | 44.17 | Step 1: In a container large enough to hold the entire batch, add the Water of Part A, with rapid mixing, add the Avicel RC-591 of Part A and mix until free from lumps. |
| Avicel RC-591 | 2.00 | |
| Part B Ingredients | | |
| Disodium EDTA | 0.10 | Step 2: Add the ingredients of Part B to the batch of Step 1 and mix until dispersed. Begin heating the aqueous phase to 158-167° F. (70-75° C.) with mixing. |
| Ganex P-904 LC | 0.80 | |
| Glycerin, USP | 2.50 | |
| Sunspheres PGL | 8.00 | |
| Part C Ingredients | | |
| Octocrylene, USP | 8.00 | Step 3: In a separate container, add the ingredients of Part C and heat to 158-167° F. (70-75° C.) with mixing until dissolved. |
| Octisalate, USP | 4.50 | |
| Homosalate, USP | 10.00 | |
| Dicaprylyl Ether | 2.00 | |
| Vitamine E, USP | 0.25 | |
| Avobenzone, USP | 3.00 | Step 4: Add the oil phase of Step 3 to the batch of Step 2 and mix until homogenous. Turn off heat and cool to at least 113° F. (45° C.). |
| Oxybenzone, USP | 6.00 | |
| Prolipid 141 | 4.50 | |
| Lanette 22 (CM) | 2.00 | |
| Cetyl Alcohol, NF | 1.00 | |
| Chlorphenesin | 0.27 | |
| Part D Ingredients | | |
| Sodium Ascorbyl Phosphate | 0.01 | Step 5: Add the Part D ingredients to the batch then slowly added the Dry-Flo to the batch and mix well. |
| Benzyl Alcohol, NF | 0.90 | |
| Dry-Flo Pure | 4.00 | |
| Part E Ingredients | | |
| Purified water, USP | Q.S. | Step 6: Q.S. the batch with water of Part E and mix well. Package accordingly. |

2. Finished Product (Concentrate+Propellant): Whipped Sunscreen Lotion SPF 50 (BOV) (Z16-016), Batch Size: 5 oz. Bag on Valve (BOV) Can

TABLE 5

| Part A Ingredients | Concentration (% w/w) | Manufacturing Directions |
| --- | --- | --- |
| Whipped Lotion Concentrate SPF 50 (Y71-098) | 98.10 | FILL CANS 98.10/1.90 AS FOLLOWS: % W/W INGREDIENT 98.10 Whipped Lotion Concentrate SPF 30 (Y71-098) 1.90 Nitrous Oxide |
| Nitrous Oxide | 1.90 | |

Appendix B. Laboratory manufacturing process for Whipped After Sun Lotion (Finished Product: Z16-023, Concentrate: Z16-020)

1. Concentrate (Base Formulation): Whipped After Sun Lotion Concentrate (Z16-020), Batch Size: 1000 g

TABLE 6

| | Concentration (% w/w) | Manufacturing Directions |
|---|---|---|
| Part A Ingredients | | |
| Purified water, USP | 74.825 | Step 1. In a container large enough to |
| Glycerin, USP | 3.00 | hold the entire batch, add the ingredients |
| *Aloe Vera* Gel 40:1 | 0.375 | of Part A to the Water of Part A and heat to 70-75° C. (158-167° F.) with mixing. |
| Part B Ingredients | | |
| Promulgen G | 4.00 | Step 2: In a separate container, combine |
| Cetyl Alcohol, NF | 2.00 | the ingredients of Part B and heat to 70- |
| TegoCare 165 (formerly Lipomulse 165) | 3.00 | 75° C. (158-167° F.) with mixing. |
| Chlorphenesin | 0.20 | |
| Dimethicone, NF 350 cst | 0.50 | Step 3: Add the oil phase of Step 2 to the aqueous phase of Step 1 with rapid mixing |
| Oxynex ST Liquid | 0.50 | using a high speed blade. |
| Vitamin E, USP | 0.50 | Cool batch to 45-50° C. (113-122° F.) with |
| Actiplex 5224 Lipo M (# 405224-17) | 0.10 | mixing. Change mixer to 3 prong prop. |
| Permethyl 101A | 5.00 | |
| Isopropyl Palmitate | 5.00 | |
| Part C Ingredients | | |
| DL-Panthenol 50L | 0.10 | Step 4: Add the ingredients of Part C to |
| Benzyl Alcohol, NF | 0.70 | the batch with mixing and cool to less |
| Fragrance, Mango SZ-1010 Mod 1 | 0.20 | than 36° C. (100° F.). |
| Part D Ingredients | | |
| Purified water, USP | Q.S. | Step 5: Q.S. the batch with water of Part D and mix well. Package accordingly. |

2. Finished Product (Concentrate+Propellant): After Sun Whipped Lotion (BOV) (Z16-023), Batch Size: 5 oz. Bag on Valve (BOV) Can

TABLE 7

| Part A Ingredients | Concentration (% w/w) | Manufacturing Directions |
|---|---|---|
| Whipped After Sun Concentrate (Z16-020) | 98.10 | FILL CANS 98.10/1.90 AS FOLLOWS: % W/W INGREDIENT 98.10 Whipped After Sun Concentrate (Z16-020) |
| Nitrous Oxide | 1.90 | 1.90 Nitrous Oxide |

Other Embodiments

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A thermal stable whipped formulation expelled from a pressurized package, the formulation comprising one or more active agents and one or more thermal stabilizing agents co-mingled with a gas propellant prior to being filled under pressure into said package and prior to being expelled from said package; wherein said gas propellant is added in sufficient amounts to be dispersed in the formulation;
   wherein said package, prior to the whipped formulation being expelled from said package, is under sufficient pressure suitable to expel said formulation as a whipped formulation upon application of external force on said formulation in said package; wherein said thermal stabilizing agent(s) comprises behenyl alcohol at about 1.2% w/w to about 8.7% w/w of said formulation and a mixture of cellulose gum and microcrystalline cellulose based product;
   wherein said formulation remains stable after the formulation is expelled from the package after storage for at least one day to up to one month at a temperature up to about 50° C.

2. The formulation of claim 1, wherein said formulation is for topical application.

3. The formulation of claim 1, wherein said formulation is an emulsion.

4. The formulation of claim 1, wherein said formulation is a sunscreen and said one or more active agents include one or more sunscreen active agents.

5. The formulation of claim 1, wherein said mixture of cellulose gum and microcrystalline cellulose-based product comprises microcrystalline cellulose and carboxymethyl cellulose.

6. The formulation of claim 1, wherein said formulation has at least about 60% of the gas bubbles at ≤100 μm, after the formulation is expelled from the package.

7. The formulation of claim 1, wherein said formulation has at least about 40% of the gas bubbles at ≤60 μm, after the formulation is expelled from the package.

8. A method of preparing a whippable formulation, comprising:
- (a) Filling a formulation into a package comprising one or more active agents and one or more thermal stabilizing agents, said one or more active agents and one or more thermal stabilizing agents co-mingled with a gas propellant prior to being filled under pressure into said package;
- wherein said propellant is added in sufficient amounts to be dispersed in the formulation;
- the gas propellant being dispersed in the formulation by rapidly mixing the formulation, with all ingredients blended, in a high shear, continuous-flow, high-pressure whipping head, pressurized under controlled temperature, rate of flow, and pressure, which rapidly mixes the formulation with a series of infusion gas injector ports controlling the gas propellant pressure and rates;
- wherein said pressurized package is under sufficient pressure suitable to maintain the gas propellant dispersed in the formulation; and
- wherein said pressurized package is under sufficient pressure to expel said formulation as a whipped formulation upon application of external force on said formulation in said package; wherein said thermal stabilizing agent(s) comprises behenyl alcohol at about 1.2% w/w to about 8.7% w/w of said formulation and a mixture of cellulose gum and microcrystalline cellulose based product.

9. The method of claim 8, wherein said package comprises a pressure generating and maintaining component, wherein said component comprises one or more gas and/or liquid propellants which are not co-mingled with the formulation.

10. The method of claim 8, wherein said whipped formulation is a sunscreen whipped formulation.

11. A pressurized package comprising a whippable formulation, the formulation comprises one or more active agents and one or more thermal stabilizing agents, said formulation being co-mingled with a gas propellant prior to being filled under pressure into said package;
- wherein said propellant is added in sufficient amounts to be dispersed in the formulation;
- wherein said pressurized package is under sufficient pressure suitable to maintain the gas propellant dispersed in the formulation; and
- wherein said pressurized package is under sufficient pressure to expel said formulation as a whipped formulation upon application of external force on said formulation in said package; wherein said thermal stabilizing agent(s) comprises behenyl alcohol at about 1.2% w/w to about 8.7% w/w of said formulation and a mixture of cellulose gum and microcrystalline cellulose based product;
- wherein said formulation remains stable after the formulation is expelled from the package after storage for at least one day to up to one month at a temperature up to about 50° C.

12. The package of claim 11, wherein said formulation is a sunscreen formulation and said one or more active agents include one or more sunscreen active agents.

13. A whipped formulation expelled from a package of claim 11.

* * * * *